United States Patent [19]

Piwnica-Worms

[11] Patent Number: 5,403,574
[45] Date of Patent: Apr. 4, 1995

[54] EVALUATION AND TREATMENT OF THE MULTIDRUG RESISTANCE PHENOTYPE

[75] Inventor: David R. Piwnica-Worms, Wellesley, Mass.

[73] Assignee: Brigham and Women's Hospital, Boston, Mass.

[21] Appl. No.: 904,363

[22] Filed: Jun. 26, 1992

Related U.S. Application Data

[63] Continuation-in-part of Ser. No. 719,714, Jun. 26, 1991.

[51] Int. Cl.$^6$ .................. A61K 43/00; A61K 31/28; G01N 23/00; G01N 33/48
[52] U.S. Cl. .................. 424/1.65; 514/492; 514/836; 436/57; 436/63
[58] Field of Search ............... 424/1.1, 450, 572, 573, 424/1.65, 4, 9, 617; 558/302; 514/492, 836; 436/57, 63, 64; 534/10, 14

[56] References Cited

U.S. PATENT DOCUMENTS

| | | | |
|---|---|---|---|
| 4,452,774 | 6/1984 | Jones et al. | 424/1.1 |
| 4,837,306 | 6/1989 | Ling et al. | 530/387 |
| 4,872,561 | 10/1989 | Jones et al. | 206/569 |
| 4,894,445 | 1/1990 | Carpenter, Jr. et al. | 534/14 |
| 5,025,020 | 6/1991 | Van Dyke | 514/280 |
| 5,186,923 | 2/1993 | Piwnica-Worms et al. | 424/9 |

OTHER PUBLICATIONS

Ames, G. F., "Bacterial Periplasmic Transport Systems: Structure, Mechanism, and Evolution", *Ann. Rev. Biochem.* 55:397 (1986).

Bitonti, A. J. et al., "Reversal of Chloroquine Resistance in Malaria Parasite *Plasmodium falciparum* by Desipramine", *Science* 242:1301–1303 (1988).

Bradley, G. et al., "Mechanism of Multidrug Resistance", *Biochim. et Biophys. Acta* 948:87–128 (1988).

Broxterman, H. J. et al., "Induction by Verapamil of a Rapid Increase in ATP Consumption in Multidrug-Resistant Tumor Cells", *FASEB J.* 2:2278–2282 (1988).

Cano-Gauci, D. F. et al., "Action of Calcium Antagonists on Multidrug Resistant Cells", *Biochem. Pharmacol.* 36 (13):2115–2123 (1987).

Chen, C. et al., "Internal Duplication and Homology with Bacterial Transport Proteins in the mdr1 (P-Glycoprotein) Gene from Multidrug-Resistant Human Cells", *Cell* 47:381–389 (1986).

Cornwell, M. M et al., "Certain Calcium Channel Blockers Bind Specifically to Multidrug-resistance Human KB Carcinoma Membrane Vesicles and Inhibit Drug Binding to P-glycoprotein", *J. Biol. Chem.* 262(5):2166–2170 (1987).

Dalton, W. S. et al., "Drug-Resistance in Multiple Myeloma and Non-Hodgkin's Lymphoma: Detection of P-Glycoprotein and Potential Circumvention by Addition of Verapamil to Chemotherapy", *J. Clin. Oncol.* 7(4):415–424 (1989).

Efferth, Th. et al., "Rapid Detection Assays for Multidrug Resistance", *Arzneim.-Forsch./Drug Res.* 38(12):1771–1774 (1988).

Ford, J. M. et al., "Pharmacology of Drugs that Alter Multidrug Resistance in Cancer", *Pharmacol. Reviews* 42(3):155–199 (1990).

(List continued on next page.)

Primary Examiner—Robert L. Stoll
Assistant Examiner—Lara E. Chapman
Attorney, Agent, or Firm—Sterne, Kessler, Goldstein & Fox

[57] ABSTRACT

The present invention relates to methods for detecting the multidrug resistance phenotype in vivo and in vitro. The invention particularly relates to methods of diagnosing the multidrug resistance phenotype by imaging, particularly scintigraphic imaging, in solid tumors in vivo or in tumors and biopsies in vitro. The methods of the present invention allow the diagnosis of multidrug-resistant tumor and other multidrug-resistant phenotypes without invasive surgical methods. The present invention is also directed to methods of treating multidrug resistant tumors with novel agents that bind to P-glycoprotein. The novel compounds of the present invention are co-administered with a chemotherapeutic agent in order to enhance accumulation of the drug.

8 Claims, 10 Drawing Sheets

OTHER PUBLICATIONS

Gerlach, J. H. et al., "Homology between P-glycoprotein and a Bacterial Haemolysin Transport Protein Suggests a Model for Multidrug Resistance", *Nature* 324:485–489 (1986).

Gottesman, M. M. et al., "The Multidrug Transporter, a Double-edged Sword", *Biol Chem.* 263(25):12163–12166 (1988).

Gottesman, M. M. et al., "Resistance to Multiple Chemotherapeutic Agents in Human Cancer Cells", *TIPS Rev.* 9(2):54–58 (1988).

Gros, P. et al., "Mammalian Multidrug Resistance Gene: Complete cDNA Sequence Indicates Strong Homology to Bacterial Transport Proteins", *Cell* 47:371–380 (1986).

Herweijer, H. et al., "A Rapid and Sensitive Flow Cytometric Assay for the Detection of Multidrug Resistant Cells in Human Cancer", *Invest. New Drugs* 7(4):442 [Entry 374] (1989).

Higgins, C. F. et al., "Periplasmic Binding Protein-Dependent Transport Systems; the Membrane-Associated Components", *Phil. Trans. R. Soc. Lond.* 326:353–365 (1990).

Higgins, C. F. et al., "Binding Protein-Dependent Transport Systems", *J. Bioenerg. Biomembr.* 22(4)571–592 (1990).

Higgins, C. F. et al., "A Family of Closely Related ATP-Binding Subunits from Prokaryotic and Eukaryotic Cells", *BioEssays* 8(4):111–116 (1988).

Higgins, C. F. et al., "A Family of Related ATP-Binding Subunits Coupled to Many Distinct Biological Processes in Bacteria", *Nature* 323:448–450 (1986).

Horio, M. et al., "ATP-Depenndet Transport of Vinblastine in Vesicles from Human Multidrug-Resistant Cells", *PNAS USA* 85:3580–3584 (1988).

Hyde, S. C. et al., "Structural Model of ATP-Binding Proteins Associated with Cystic Fibrosis, Multidrug Resistance and Bacterial Transport", *Nature* 346:362–365 (1990).

Juranka, P. F. et al., "P-Glycoprotein: Multidrug-Resistance and a Superfamily of Membrane-Associated Transport Proteins", *FASEB J.* 3:2583–2592 (1989).

Konen, P. L. et al., "The Multidrug Transporter: Rapid Modulation of Efflux Activity Monitored in Single Cells by the Morphologic Effects of Vinblastine and Daunomycin", *J. Histochem. Cytochem.* 27(7):1141–1145 (1989).

Krogstad, D. J. et al., "Efflux of Chrloroqhine from *Plasmodium falciparum*: Mechanism of Choloroquine Resistance", *Science*, 238:1283–1285 (1987).

Larsson, R. et al., "Pharmacological Modification of Multi-Drug Resistance (MDR) *In Vitro* Detection by a Novel Fluorometric Microculture Cytotoxicity Assay. Reversal of Resistance and Selective Cytotoxic Actions of Cyclosporin A and Verapamil on MDR Leukemia T-Cells", *Int. J. Cancer* 46:67–72 (1990).

McGrath, J. P. et al., "The Yeast STE6 Gene Encodes a Homologue of the Mammalian Multidrug Resistance P-Glycoprotein", *Nature* 340:400–404 (1989).

Piwnica-Worms, D. et al., "Enhancement by Tetraphenylborate of Technetium-99m-MIBI Uptake Kinetics and Accumulation in Cultured Chick Myocardial Cells", *J. Nuclear Medicine* 32(10):1992–1999 (1991).

Rothenberg, M. et al., "Multidrug Resistance: Molecular Biology and Clinical Relevance", *J. Natl. Cancer Ins.* 81(12):907–910 (1989).

Safa, A. R., "Photoaffinity Labeling of the Multidrug-Resistance-Related P-Glycoprotein with Photoactive Analogs of Verapamil", *PNAS USA* 85:7187–7191 (1988).

Skovsgaard, T. et al., "Chemosensitizers Counteracting Acquired Resistance to Anthracyclines and Vinca Alkaloids *In Vivo*. A New Treatment Principle", *Cancer Treatment Reviews* 11(Suppl. A):63–72 (1984).

Tsuruo, T. et al., "Overcoming of Vincristine Resistance in P388 Leukemia in Vivo and in Vitro through Enhanced Cytotoxicity of Vincristine and Vinblastine by Verapamil", *Cancer Research* 41:1967–1972 (1981).

Yoshimura, A. et al., "Novel Screening Method for Agents that Overcome Classical Multidrug Resistance in a Human Cell Line", *Cancer Letters* 50:45–51 (1990).

McGraw-Hill Dictionary of Chemical Terms, 1984, p. 32.

R1, R2, R3= H, OH, MeO, NH2, O-CH2-O, SO2, EthO, Acetyl, Acetamide, CN
n=0-20
X=Re, Tc, Fe, Co, Mn
y=2-6

3-, 4-, 5-trimethoxyphenylisonitrile

3-, 4-dimethoxybenzylisonitrile

3-, 4-dimethoxyphenethylisonitrile 4-acetylphenylisonitrile

3-, 4-, 5-trimethoxyphenethylisonitrile

3-, 4-O-CH2-O-phenylisonitrile

EVALUATION AND TREATMENT OF THE MULTIDRUG RESISTANCE PHENOTYPE

STATEMENT AS TO RIGHTS TO INVENTIONS MADE UNDER FEDERALLY-SPONSORED RESEARCH AND DEVELOPMENT

Part of the work leading to this invention utilized U.S. Government funds. The U.S. Government has certain rights in this invention.

CROSS REFERENCE TO RELATED APPLICATIONS

This application is a continuation-in-part application of U.S. Ser. No. 07/719,714, filed Jun. 26, 1991, pending.

BACKGROUND OF THE INVENTION

1. Field of the Invention

The present invention relates to methods for detecting the multidrug resistance phenotype in vivo and in vitro. The invention particularly relates to methods of diagnosing the multidrug resistance phenotype by imaging, particularly scintigraphic imaging, in solid tumors in vivo or in tumors and biopsies in vitro. The methods of the present invention allow the diagnosis of multidrug-resistant tumors and other multidrug-resistant phenotypes without invasive surgical methods.

The invention also relates to methods to increase the net uptake of drugs, and especially chemotherapeutic drugs, into cells and particularly to cells in vivo in malignant tumors. The invention is directed to new chemosensitizing agents and their use to enhance the uptake of various chemotherapeutic drugs. The methods of the present invention allow therapy of patients with multidrug resistant tumors. The methods of therapy of the present invention use compounds that interact with the multidrug resistance transport protein. The invention is directed to multidrug-resistance reversal agents that inhibit the cellular efflux of chemotherapeutic and other cytotoxic drugs in vivo and in vitro.

2. Description of the Background Art

A. ATP Binding Cassette Transport Proteins (Higgins, C. F. et al., *Bioessays* 8:11 (1988); Ames, G. F., *Ann. Rev. Blochem.* 55:397 (1986); Higgins, C. F. et al., *J. Bioenerg. Biomembr.* 22:571 (1990); Hyde, S. C. et al., *Nature* 396:362 (1990); Higgins, C. F. et al., *Phil. Trans. R. Soc. Lond. B* 326:353 (1990)).

A large number of cellular proteins bind ATP, many of which utilize the free energy of ATP hydrolysis to drive particular biological reactions. Several of these comprise a subfamily, the members of which share considerable sequence homology. The region of homology extends over 200 amino acids. In several of the proteins the conserved domain comprises nearly the entire polypeptide. In others the conserved domain is only one segment of a multi-domain protein. These proteins include the multidrug resistance P-glycoprotein, the product of the White locus of Drosophila, procaryotic proteins associated with membrane transport, cell division, nodulation and DNA repair, the STE-6 gene product that mediates export of yeast α-factor mating pheromone, pfMDR that is implicated in chloroquine resistance of the malarial parasite, and the product of the cystic fibrosis gene (CFTR).

There are two short amino acid sequence motifs which are present in most if not all nucleotide binding proteins. The subfamily of ATP binding proteins that are relevant to this invention are distinct from all other ATP binding proteins in that they share considerably more sequence identity than is simply required for nucleotide binding. Other ATP binding proteins may possess the consensus nucleotide binding motifs but otherwise share no significant sequence similarity. This implies that the subfamily of proteins shares common functions in addition to the ability to bind ATP. Many of the proteins of the subfamily and those which are best characterized, are components of an active transport system which mediates the transport of molecules across the cytoplasmic membrane. They are recognized in the art as ATP-binding cassette superfamily of transport proteins (Hyde, S., et al., *Nature* 346:362 (1990)).

Several nucleotide binding protein-dependent transfer systems have been characterized in procaryotes. Each system requires a substrate binding protein located in the periplasm that provides a primary receptor for transport. The system also contains two integral membrane proteins that transport substrates across the membrane. The system further contains two peripheral membrane proteins thought to be located on the inner surface of the cytoplasmic membrane. These peripheral membrane proteins are members of the subfamily of bacterial and eucaryotic ATP binding proteins relevant to this invention.

P-glycoprotein is a eucaryotic four-domain protein consisting of two hydrophobic domains and two ATP binding domains. Besides the conserved ATP binding domains, there is a great deal of similarity between P-glycoprotein and bacterial binding protein dependent transport systems. The organization of this protein is remarkably similar to that of bacterial transport systems. The two hydrophobic domains in P-glycoprotein are homologous to each other. The same is true for the two hydrophobic components of the binding protein system.

There are also a number of differences. First, the P-glycoprotein consists of four domains encoded as a single polypeptide, whereas in bacteria the equivalent domains are on separate polypeptides. Second, P-glycoprotein pumps drugs out of the cell whereas the binding protein dependent transport system mediates uptake. Third, protein dependent transport systems require a periplasmic component which serves as the initial substrate binding site and delivers substrate to the membrane component. However, as far as is known there is no equivalent component which interacts with the P-glycoprotein. Fourth, there is an important difference between P-glycoprotein and the bacterial transport systems in substrate specificity. The bacterial systems are relatively specific and there is a separate system for each substrate. In contrast, P-glycoprotein exhibits a very broad specificity, handling a range of apparently unrelated drugs. However, most of the differences may be trivial rather than fundamental mechanistic differences. It is not uncommon for functions carried out by separate polypeptide chains in procaryotes to be fused into a single multifunctional protein in eukaryotes. Further, a small change in the organization of a transport system could promote efflux rather than uptake. Finally, the periplasmic components of bacterial systems can be viewed as a specific adaptation to the fact that bacteria have a periplasm.

The similarity between P-glycoprotein and the bacterial active transport system may be relevant to the mechanisms of multidrug resistance in eucaryotic cells.

All available evidence is compatible with the view that P-glycoprotein is a eucaryotic transport system. Most chemotherapeutic drugs are lipophilic and can enter the cells passively. In multidrug-resistant cells, the intracellular concentration of these drugs is reduced in an energy-dependent manner. The most reasonable explanation for these findings is that P-glycoprotein is an active transport system, pumping drugs out of the cell.

B. Multidrug Resistance

One problem facing the cell biologist and oncologist is the tendency of cultured cells and tumors in patients to exhibit simultaneous resistance to multiple chemically unrelated chemotherapeutic agents. Tissue culture cells can be selected for resistance to a variety of drugs such as colchicine, doxorubicin (Adriamycin), actinomycin D and vinblastine. Increasing the concentration of the selecting agent in multiple small single steps results in high levels of cross resistance to these agents as well as many other drugs including other anthracyclines, Vinca alkaloids and epipodophyllotoxins (Gottesman, M. M. et al., *J. Biol. Chem.* 263:12163 (1988)).

Resistance of malignant tumors to multiple chemotherapeutic agents is a major cause of treatment failure (Wittes et al., *Cancer Treat. Rep.* 70:105 (1986); Bradley, G. et al., *Biochim. Biophys. Acta* 948:87 (1988); Griswald, D. P. et al., *Cancer Treat. Rep.* 65(S2):51 (1981); Osteen, R. T. (ed.), *Cancer Manual*, (1990)). Tumors initially sensitive to cytotoxic agents often recur or become refractory to multiple chemotherapeutic drugs (Riordan et al., *Pharmacol. Ther.* 28:51 (1985); Gottesman et al., *Trends Pharmacol. Sci.* 9:54 (1988); Moscow et al., *J. Natl. Cancer Inst.* 80:14 (1988); Croop, J. M. et al., *J. Clin. Invest.* 81:1303 (1988)). Cells or tissues obtained from tumors and grown in the presence of a selecting cytotoxic drug can result in cross-resistance to other drugs in that class as well as other classes of drugs including anthracyclines, Vinca alkaloids, and epipodophyllotoxins (Riordan et al., *Pharmacol. Ther.* 28:51 (1985); Gottesman et al., *J. Biol. Chem.* 263:12163 (1988)). Thus, acquired resistance to a single drug results in simultaneous resistance to a diverse group of drugs that are structurally and functionally unrelated.

The characteristics of the multidrug resistance phenotype have been analyzed by studies on normal and tumor cell lines isolated for resistance to selected cytotoxic drugs. One major mechanism of multidrug resistance in mammalian cells involves the increased expression of the 170-kDa plasma membrane glycoprotein, P-glycoprotein (for review, Juranka et al., *FASEB J* 3:2583 (1989); Bradley, G. et al., *Biochem. Biophys. Acta* 948:87 (1988)). Transfection of cloned P-glycoprotein genes into drug-sensitive cell lines has confirmed that an increased expression of P-glycoprotein is sufficient to cause multidrug resistance in experimental systems (i.e., Gros, P. et al., *Nature* 323:728 (1986)).

The nucleotide sequence of multidrug resistance cDNA (Gros, P. et al., *Cell* 47:371 (1986); Chen, C. et al., *Cell* 47:381 (1986)) indicates that it encodes a polypeptide similar or identical to P-glycoprotein and that these are members of the highly conserved class of membrane proteins similar to bacterial transporters and involved in normal physiological transport processes.

The multidrug resistance P-glycoprotein may function normally to extrude as yet unknown physiological substrates out of cells by an energy-dependent process (Arceci, R. J. et al., *PNAS USA* 85:4350 (1988)) in normal tissues. The gene is amplified and consequently overexpressed in malignant tissues. It is thus believed that by transporting chemotherapeutic agents out of the cells, P-glycoprotein renders tumors resistant to chemotherapy.

C. Visual Assay of Multidrug Resistance

Multidrug resistance has been detected in vitro in single cell suspensions and in cell monolayers. Yoshimura et al., (*Cancer Letters* 50:45 (1990)) used the uptake of rhodamine dye to screen for agents that overcome multidrug resistance in a cell line ("reversing agents"). The dye is accumulated in multidrug-resistant cells at a lower rate than it is accumulated in non-resistant cells and thus multidrug-resistant cells can be distinguished from non-resistant cells by comparing intracellular dye levels.

In this study, the authors monitored dye levels in multidrug-resistant cells in the presence and absence of verapamil, a known chemosensitizer (reversing agent used in chemotherapy to facilitate the uptake of a chemotherapeutic drug in drug-resistant tumor cells), and found that the dye accumulated to normal levels when the multidrug resistance phenotype was reversed with verapamil. The dye was administered to cells in a confluent monolayer. The cells were then either washed, solubilized, and the dye detected with a fluorescence spectrometer, or scanned in microtitre wells with a fluorescence microplate reader.

Efferth et al. (*Arzneim-Forsch* 38:1771 (1988)) also developed an in vitro assay to detect the multidrug resistance phenotype. They compared the levels of rhodamine dye in a cell sample with the levels of dye found in a control sample of normal cells. The dye was detected by forming a single cell suspension, pipetting the suspension onto slides, administering the dye to the cells on the slide and detecting dye uptake of cells on the slide.

Herweijer et al. (*Invest New Drugs* 7:442 (1989)) used on-line flow cytometry to detect cells with the multidrug resistance phenotype in a single cell suspension. The uptake kinetics of a fluorescent drug were measured on line first in the absence and then in the presence of a reversing agent.

Konen et al. (*J. Histochem. Cytochem.* 37:1141 (1989)) assayed efflux activity of the multidrug resistance transport system using fluorescence microscopy to monitor the accumulation of drugs in single cultured cells that were transformed with multidrug resistance DNA. They showed that the efflux pathway was inhibited when the cells were incubated with verapamil.

D. Scintigraphic Imaging with Hexakis (R-isonitrile) Technetium Complexes

Hexakis (R-isonitrile) technetium (I) complexes (where R is alkyl, substituted alkyl, aryl, or substituted aryl) are a class of low valence technetium ($^{99m}$Tc) coordination compounds empirically designed as clinical myocardial perfusion imaging agents (Jones, A. G. et al., *Int. J. Nucl. Med. Biol.* 11:225 (1984), Holman, B. L., et al., *J. Nucl. Med.* 25:1350 (1984), Holman, B. L., et al., ibid 28:13 (1987), Sporn, V., *Clin. Nucl. Med.* 13:77 (1988)). Conceived to be used in a manner similar to thallus chloride for the noninvasive evaluation of coronary artery disease, the compounds exploit the more favorable emission characteristics of $^{99m}$Tc for applications in clinical imaging (Strauss, H. W., et al., *Radiology* 160:577 (1986), Deutsch, E., et al., *Science* 214:85 (1981)). Chemical analysis of these complexes with the ground state $^{99}$Tc isotope shows them to be monovalent cations with a central Tc(I) core octahedrally surrounded by six identical ligands coordinated through the isonitrile carbon. The terminal R groups, when bound to the technetium, encase the metal with a sphere of lipophilicity (Jones, A. G., et al., *Int. J. Nuc. Med. Biol.* 11:225 (1984), Mousa, S. A., et al., *J. Nuc. Med.* 28:1351 (1987)).

These complexes are sufficiently lipophilic to partition into and through the hydrophobic core of biological membranes, but also combine this property with a delocalized cationic charge which renders the compounds responsive to the plasma and mitochondrial transmembrane potentials. This combination of lipophilicity and delocalized charge produces an unusual property for these pharmaceuticals. Unlike tissue binding of many other pharmaceuticals that depend on highly specific binding sites (high affinity receptors), these pharmaceuticals have a non-specific uptake mechanism. However, tissue interaction is highly specific for those tissues with high plasma membrane potentials, high mitochondrial membrane potentials, high mitochondrial content, or combinations of the above.

Because uptake of these compounds by tissues is non-specific, any living cell (and potentially, any tissue type) can retain the compounds. A further advantage is that the compounds have been shown to be safe in humans as diagnostic pharmaceuticals while maintaining the unique combination of properties that allow them to respond to membrane potential. Conversely, other classes of lipophilic cations or fluorescent probes of membrane potential (e.g., rhodamine 123) have been shown to be toxic to cells and mitochondria (Bernel, et al., *Science* 218:1117 (1982), Emaus, R. K., et al., *Biochim. Biophys. Acta* 850:436 (1986), Gear, A. R. L., *J. Biol. Chem.* 249:3628 (1974)). These compounds have not been injected into humans.

E. Model for P-Glycoprotein Function

Based on the information obtained from amino acid sequence analysis of P-glycoprotein from various mammalian cells, a model for P-glycoprotein function has been suggested (Bradley et al., *Biochimica et Biophysica Acta* 948:87 (1988)). The model suggests that P-glycoprotein forms a channel in the plasma membrane and transports drugs out of cells using energy derived from ATP hydrolysis. In one version of the model, P-glycoprotein binds drugs directly and then removes them from the cell. It is suggested that, since transfection of a P-glycoprotein cDNA clone into drug sensitive cells results in cross-resistance to structurally unrelated drugs, the P-glycoprotein molecule may have binding sites for a diverse group of drugs.

There is other experimental evidence to support a drug binding function for P-glycoprotein. First, membrane vesicles from drug resistant cell lines have been shown to overexpress a protein of 150-180 kilodaltons that specifically binds vinblastine (Safa et al., *J. Biol. Chem.* 261:6137 (1986); Cornwell et al., *Proc. Natl. Acad. Sci. USA* 83:3847 (1986)). Labeling is inhibited by drugs which are cross-resistant with vinblastine in these cells. This suggests that the drugs may be competing for either the same binding site or a closely adjacent binding site. The 150-180 kilodalton protein that binds vinblastine was immunoprecipitated with a monoclonal antibody against P-glycoprotein (Cornwell, M. M., et al., *J. Biol. Chem.* 262:2166 (1987)).

Further evidence that drug binding is involved in the function of P-glycoprotein in multidrug resistant cells is derived from the study of chemosensitizers/reversing agents (see also text below). Many of these agents inhibit photoaffinity labeling of P-glycoprotein by vinblastine analogs (Akiyama, S. I., et al., *Mol. Pharm.* 33:144 (1988)). It thus appears that the mechanism of action of reversing agents may be to inhibit toxic drug binding to P-glycoprotein.

However, it appears that there may be multiple drug binding domains in the P-glycoprotein because, first, the inhibition of the vinblastine analog binding was not equivalent to the ability to reverse multidrug resistance for several compounds, and, second, drugs that are involved in the multidrug resistance phenotype do not necessarily compete for the vinblastine analog binding site in vesicles from multidrug-resistant cells (Cornwell et al., M. M., et al., *J. Biol. Chem.* 262:2166 (1987); Akiyama, S. I., et al., *Mol. Pharm.* 33:144 (1988)).

In an alternative version of the model for P-glycoprotein function, a drug binding protein is transported out of cells by a P-glycoprotein pump. Drugs may bind irreversibly to this protein, and the entire drug-protein complex may then be removed from the cell.

Direct binding of drug analogs to the P-glycoprotein has been observed. P-glycoprotein can be labeled directly by a photoactive vinblastine analog in a saturable manner. This photoaffinity labeling can be inhibited by drugs such as daunomycin or vincristine, as well as several chemosensitizing agents such as verapamil, quinidine, reserpine, and azidopine (Gottesman, M. M., et al., *Trends Pharmacol. Sci.* 9:54 (1988)). Conversely, the labeling of P-glycoprotein by a photoactive analog of verapamil can be inhibited by some, but not all, drugs involved in the MDR phenotype (Safa, A. R., *Proc. Natl. Acad. Sci. USA* 85:7187 (1988)). Because these drugs and reversing agents may inhibit binding to P-glycoprotein, this suggests that a common binding site may be involved. Accordingly, a mechanism of reversal of the MDR phenotype by reversing agents/chemosensitizers may be explained on the basis of competition for drug binding, which results in decreased efflux of drugs which are taken up by the cell and thus a higher intracellular level of such drugs, such as chemotherapeutic drugs, in cells that are multidrug resistant.

F. Pharmacological Reversal of Multidrug Resistance by Chemosensitizers

Since recent studies have shown that P-glycoprotein associated multidrug resistance occurs clinically (Yoshimura, A., et al., *Cancer Lett.* 50:45 (1990)), strategies designed either to block expression or to circumvent this form of drug resistance are being sought by researchers in the field of cancer therapeutics. Particularly desirable are agents that inhibit P-glycoprotein activities at concentrations with little or no cytotoxic effect. These would be used in overcoming multidrug resistance when they are administered in combination with other anti-cancer drugs during clinical chemotherapy.

The following parameters have been used to screen agents that overcome multidrug resistance: (1) enhanced cytotoxicity of anti-cancer drugs to multidrug resistant cells; (2) enhanced accumulation of anti-cancer drugs in multidrug resistant cells; (3) inhibition of photoaffinity labeling of P-glycoprotein with photoanalogs of anti-cancer drugs and resistance modifiers; and (4) inhibition of binding of vinblastine or vincristine to membrane vesicles from multidrug resistant cells (Yoshimura et al., A., et al., *Cancer Lett.* 50:45 (1990)).

The chemosensitizers described to date may be grouped into six broad categories: (1) calcium channel blockers; (2) calmodulin antagonists; (3) noncytotoxic anthracycline and Vinca alkaloid analogs; (4) steroids and hormonal analogs; (5) miscellaneous hydrophobic cationic compounds; and (6) cyclosporines. Although these compounds share only broad structural similarities, most are extremely lipophilic, and those in the first five groups are all heterocyclic, amphipathic substances (Ford, J. M., et al., *Pharmacol. Rev.* 42:155 (1990)).

Clinical Relevance of Multidrug Resistance and Reversing Agents

With respect to human malignancy, an important question is the physiologic relevance of P-glycoprotein. Specific questions are whether multidrug resistance based on P-glycoprotein overexpression occurs in malignancy, and if it does occur, what is its relation to the success of chemotherapeutic treatment. Increased levels of P-glycoprotein have been seen in some late stage ovarian carcinomas (Bell, D. R., et al., *J. Clin. Oncol.* 3:311 (1985)). Increased levels of P-glycoprotein or P-glycoprotein messenger RNA have been detected in all forms of human cancers, including leukemias, lymphomas, sarcomas, and carcinomas (Goldstein, L. J., et al., *J. Natl. Canc. Inst.* 81:116 (1989)). An increased level of P-glycoprotein was observed in tumor biopsies obtained after relapse during chemotherapy, compared with tumor biopsies obtained before the treatment. However, in other instances, relatively high levels of P-glycoprotein were seen in some tumors even before chemotherapy. Thus, P-glycoprotein occurs in human malignancy. However, the relationship to the response to chemotherapy is not yet clear.

The possibility of reversing the MDR phenotype using chemosensitizers to increase the intracellular accumulation of chemotherapeutic agents is being explored (Juranka, P. F., et al., *FASEB J.* 3:2583 (1989)). Verapamil has been used with some success in multiple myeloma patients who no longer responded to salvage chemotherapy (Dalton, W. S., et al., *J. Clin. Oncol.* 7:415 (1989)). This response to verapamil, in addition to the regular chemotherapeutic drugs, appears to depend upon the tumor cells expressing a significant level of P-glycoprotein. It has also been pointed out that in monkeys infected with chloroquine resistant malaria parasites, treatment was improved in the presence of a chemosensitizer (Juranka, P. F., et al., *FASEB J.* 3:2583 (1989)).

Interaction of Chemosensitizers with P-Glycoprotein

Chemosensitizers appear to act by directly affecting the function of P-glycoprotein. For example, labeled vinblastine accumulated in P-glycoprotein enriched membrane vesicles in multidrug resistant cells in a specific saturable temperature-dependent manner not observed in vesicles from either drug sensitive cells or multidrug resistant revertants to sensitivity. Accumulation could be inhibited by excess unlabeled vinblastine, vincristine and verapamil (Cornwell, M. M., et al., *J. Biol. Chem.* 261:7921 (1986)).

In other studies, photoactive analogs of vinblastine that irreversibly bind to multidrug resistant cell membrane fractions were used to identify vinblastine binding proteins. A 150–180 kilodalton photoaffinity labeled membrane protein, specific to multidrug resistant cell lines, was immunoprecipitated with an antibody that also precipitated P-glycoprotein. Further, photoaffinity labeling of a 170 kilodalton membrane protein which was immunoprecipitated by a monoclonal antibody against P-glycoprotein was inhibited by the presence of verapamil (Cornwell, M. M., et al., *Proc. Natl. Acad. Sci. USA* 83:3847 (1986); Cornwell, M. M., et al., *J. Biol. Chem.* 262:2166 (1987); Safa, A. R., et al., *J. Biol. Chem.* 261:6137 (1986)). Other studies have shown the competitive inhibition of the binding of chemotherapeutic agents by chemosensitizers (Ford, J. M., et al., *Pharmacol. Rev.* 42:155 (1990)). The results of these studies suggest that Vinca alkaloids, colchicine, and perhaps anthracyclines bind to P-glycoprotein, and that certain chemosensitizers compete for either a common drug binding site, for overlapping sites, or for sites that cause allosteric changes resulting in inhibition of the binding of other drugs.

Some chemosensitizers have been shown to bind to membranes enriched for P-glycoprotein, and this binding was inhibited by other chemosensitizers and by chemotherapeutic drugs (Ford, J. M., et al., *Pharmacol. Rev.* 42:155 (1990)). Many studies have shown that chemosensitizers may be substrates for the P-glycoprotein transport system, supporting the hypothesis that the mechanism of chemosensitization is as a competitive ligand for a site on the P-glycoprotein (Ford, J. M., et al., *Pharmacol. Rev.* 42:155 (1990)).

SUMMARY OF THE INVENTION

I. Diagnostic Imaging and Detection of Multidrug Resistance

The present invention is based on the unexpected discovery that the lipophilic cationic gamma-emitting imaging agent, hexakis (2-methoxyisobutyl isonitrile) technetium-99m (I) (Tc-MIBI), is transported out of cells against a concentration gradient by P-glycoprotein, the product of the multidrug-resistance gene and a member of the family of ATP-binding cassette transport proteins. In cells over-expressing the multidrug resistance gene, net accumulation of Tc-MIBI is very low compared to the net accumulation in cells that do not overexpress the multidrug resistance gene.

This unexpected discovery combined with the history of the clinical use of Tc-MIBI as a whole body imaging agent with no toxic activity at imaging doses, provides a method to evaluate the multidrug resistance phenotype in living cells in vivo and in tissues in vitro. This evaluation is done by administering agents that are transported by the multidrug transport system and which are detectable in living cells despite the presence of biological tissue intervening between the detection device and the cells in their in situ location. Thus, cells in the living body or in a tissue mass are detectable in situ.

In preferred embodiments of the invention, living cells are imaged. Agents that are useful in imaging procedures are administered to a patient or a tissue specimen. Imaging procedures include, but are not limited to, magnetic resonance, superconducting quantum interference device (squid), positron emission tomography, and, in highly preferred embodiments, imaging is by planar scintigraphy or single photon emission computed tomography (SPECT).

The method is applicable as a rapid and simple assay of multidrug-resistant cells in vitro and, more importantly, as an assay in instances in which presently available assay methods are impractical or impossible. For example, in excised tissues, multidrug-resistant cells are detected without the need for tissue dispersion and growth that could change the in vivo phenotype. The method is especially valuable as an in vivo assay whereby multidrug resistance tissue is detected without the need for traumatic surgery. In a highly preferred embodiment of the invention, multidrug-resistant tumors are detected in cancer patients without the need for surgery.

In preferred methods of the present invention, the multidrug resistance phenotype is detected with Tc-MIBI. At imaging doses, Tc-MIBI is without chemotoxic effects. In alternative embodiments, detection is with the broader range of technetium complexes, other non-toxic imaging agents, and other non-toxic markers that are transported by the multidrug resistance transport system and which can be detected despite the occurrence of biological tissue intervening between the cells and the imaging device.

Accordingly, the invention is directed to methods of detecting the multidrug resistance phenotype in an animal, tissues, or cells by administering an agent which is transported by the multidrug resistance transport system and which is detectable in living cells, at distances removed from the cells by the presence of intervening tissue.

The invention is particularly directed to methods of detecting the multidrug resistance phenotype in an animal, tissues, or cells by administering an imaging agent, especially a scintigraphic imaging agent, which is transported by the multidrug resistance transport system.

The invention is particularly directed to a method of assaying the multidrug resistance phenotype of solid tumors in vivo and in vitro by administering to patients, explanted tumor, or cells, an agent that is transported by the multidrug resistance transport system.

The invention is also directed to designing chemotherapy regimens by assaying the multidrug resistance phenotype in patients or their explanted tissue either prior to or during treatment.

In the assays of the present invention, the agent alone is administered to the subject (cells, tissue, or patient) and the incorporation of agent is measured. Thereafter, the agent is co-administered with a reversing agent and the incorporation of the agent is again measured. If the subject contains multidrug-resistant cells, these cells will accumulate less of the agent when the agent alone is administered than they will when the agent is administered with a reversing agent. Thus, when the two measurements are compared, greater intracellular accumulation of the agent in the presence of the reversing agent indicates the presence of multidrug-resistant cells.

The invention is also practiced with any of the family of ATP-binding transport proteins of which the multidrug resistance transport protein P-glycoprotein is a member.

II. Therapeutic Applications of Hexakis Aryl and Alkyl Isonitrile Metal Complexes The present invention, based on the unexpected discovery that Tc-MIBI is transported out of cells against a concentration gradient by P-glycoprotein, is now extended to therapy exploiting a wide variety of hexakis (alkylisonitrile) metal and hexakis (arylisonitrile) metal complexes. These hexakis metal isonitrile complexes define a new class of multidrug resistance reversal agents and direct chemotherapeutic agents useful in chemotherapeutic protocols.

Accordingly, the present invention describes the structure of metal isonitrile complexes that are designed to have a high affinity for the multidrug resistance transport protein and, as such, be potent reversal agents by inhibiting the cellular efflux of chemotherapeutic and cytotoxic drugs, as well as being chemotherapeutic agents per se.

The present invention is also directed to methods for reversing the multidrug resistance phenotype in cells comprising administering the complexes of the present invention to cells with the multidrug resistance phenotype. The administration may be in vitro or in vivo. In highly preferred embodiments of the invention, the complexes are administered to cancer patients in vivo as a means of treating tumors which have become multidrug resistant.

In certain embodiments of the invention, the complexes are designed to be cytotoxic and are administered alone. In more preferred embodiments of the invention, the complexes are coadministered with a chemotherapeutic drug. In this aspect, the complexes of the present invention act as a chemosensitizer or reversing agent causing the enhanced accumulation of the chemotherapeutic drug as a result of the reversal of the multidrug resistance phenotype.

The complexes of the present invention may also be used in vitro to study cytotoxicity in screening protocols for new cytotoxic compounds or in tissue biopsies from cancer patients to determine effective cytotoxic agents for a particular patient.

The complexes can be synthesized with both stable and radioactive core metals. In preferred embodiments of the therapeutic aspect of the invention, typical structures are hexakis isonitrile complexes of a core metal which may be, but is not limited to, rhenium or technetium. Other multiligand isonitrile complexes of copper, iron, cobalt, manganese, ruthenium, platinum, osmium, iridium, tungsten, chromium, molybdenum, nickel, rhodium, palladium, niobium and tantalum can also be synthesized. In these embodiments, all metals but technetium have stable (non-radioactive) isotopes found in nature and which are suitable for drug manufacture.

In alternative embodiments of the invention, radioactive isotopes of all the metals may be synthesized for use during drug design, for example, for performing biodistributions or for therapeutic exploitation of the radioactive emissions into cancer tissues. The side groups of these compounds are substituted alkyl and aryl isonitrile ligands.

DESCRIPTION OF THE PREFERRED EMBODIMENTS

Figure 1:
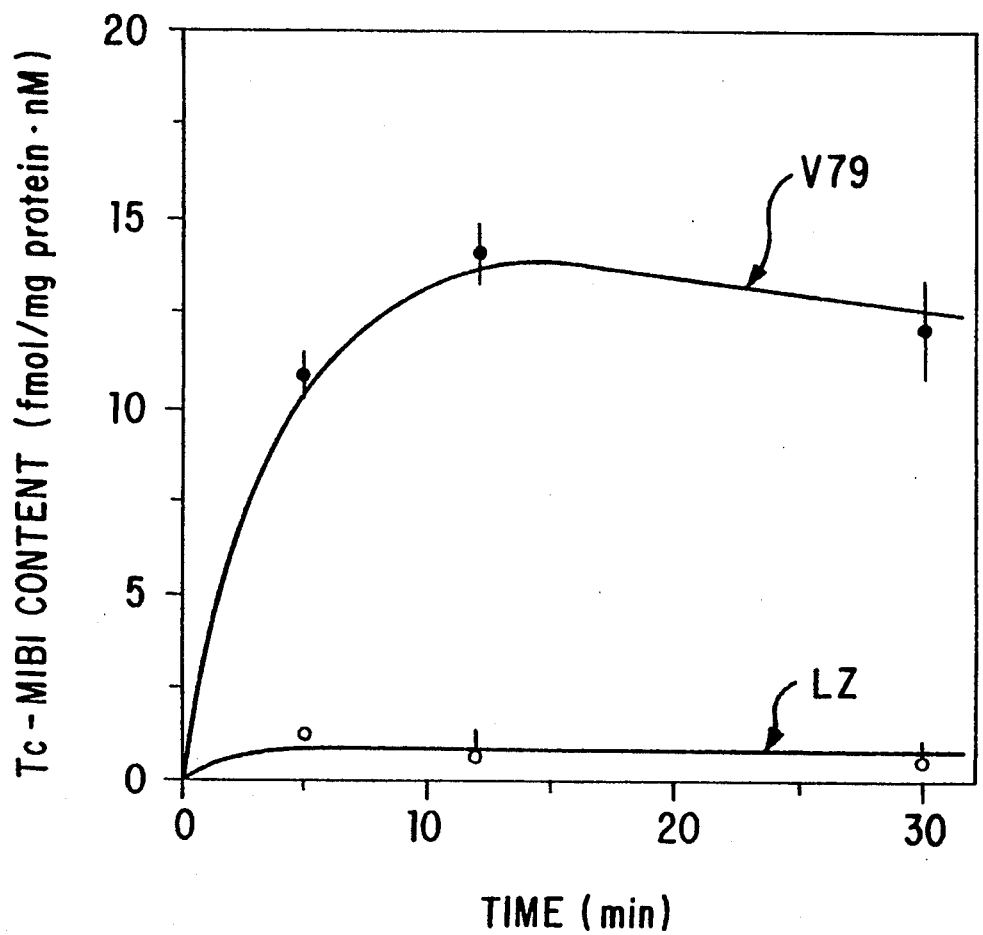
FIG. 1. Accumulation of Tc-MIBI in LZ cells (highly expressing multidrug resistance) (0) and V79 cells (modestly expressing multidrug resistance) (●). Cells were incubated in modified Earle's balanced salt solution (MEBSS) containing $^{99m}$Tc-MIBI (53 uCi/ml; 20.7 pmol/mCi) for various times and cell associated activity determined as described previously (Chiu et al., J. Nucl. Med. 31:1646-1653 (1990)). Results are expressed as fmol cellular Tc-MIBI/mg protein per nmolar extracellular Tc-MIBI. Points represent the mean ±SEM of three determinations each.

I. Diagnostic Imaging and Detection of Multidrug Resistant Living Cells

The present invention is based on the discovery that the gamma emitter, $^{99m}$Tc-MIBI, commonly used as an imaging agent for myocardial perfusion analysis, is transported out of cells by the multidrug resistance transport system. This agent, normally taken up by living cells, is actively excluded from living cells by the multidrug resistance system. Thus, when the multidrug resistance gene is overexpressed by a cell, the net accumulation of this agent is reduced compared to the levels accumulated by normal cells or cells to which have been co-administered the agent plus an agent that reverses the multidrug resistance phenotype (reversing agent). In the latter two instances, the net accumulation of the agent is higher and can be distinguished from that of multidrug-resistant cells.

Accordingly, the invention is directed to methods of detecting the multidrug resistance phenotype in an animal, tissues, or cells by administering to the animal, tissues, or cells, an agent which is transported by the multidrug resistance transport system and which is detectable in living cells, at distances removed, by the presence of intervening tissue, from the in situ location of the cells. The methods encompass measuring the intracellular accumulation of the agent in the animal, tissues, or cells, and comparing the measurement with the measurement obtained with a control that does not express the multidrug resistance phenotype.

In preferred methods of the present invention, the multidrug resistance phenotype is detected in an animal, tissues, or cells by administering to the animal, tissues, or cells, an imaging agent, particularly a scintigraphic imaging agent, which is transported by the multidrug resistance transport system. The methods then encompass imaging the animal, tissues, or cells, and comparing the image with the image obtained with a control that does not express the multidrug resistance phenotype.

In general, the invention embodies methods to assay the multidrug resistance phenotype in instances that previously required invasive in vivo surgical procedures or time-consuming in vitro outgrowth procedures. In the former instance the procedure involves trauma, often to patients already traumatized by prior treatment. In the latter instance, the phenotype of explanted cells, subject to the different selective pressures of tissue culture, and no longer subject to the in vivo selective pressures in the patient, would be subject to genotypic and phenotypic alteration that could confound diagnosis and treatment.

The present invention, therefore, embodies methods of detecting the multidrug resistance phenotype in tissues in vivo without the need for invasive procedures and in whole tissue in vitro.

In one preferred embodiment of the invention, the net cellular accumulation of the agent alone is compared with the net cellular accumulation of the agent when it is co-administered with an agent that reverses the multidrug resistance phenotype ("reversing agent"). In the presence of a reversing agent or other inhibitor, the agent is not excluded from cells, whereas in the absence of a reversing agent, relative exclusion of the agent occurs. Thus, in multidrug-resistant cells, the agent will be detected to a greater extent when administered with a reversing agent than the extent to which it is detected when administered alone. The agent is, therefore, useful as a marker for detecting the multidrug resistance phenotype.

In preferred embodiments of the invention, the agent is an imaging agent. The preferred imaging agent of the present invention is Tc-MIBI. The presence or absence of expression of the multidrug resistance phenotype is evaluated by scintigraphic imaging (either planar or SPECT) with Tc-MIBI before and after the administration of the reversing agent. The tissue significantly expressing the multidrug resistance phenotype shows little Tc-MIBI localization in the absence of the reversing agent but enhanced uptake of Tc-MIBI during infusion of the reversing agent. The tissue not expressing the multidrug resistance phenotype shows Tc-MIBI localization initially, but does not demonstrate reversing agent-induced enhancement of net uptake.

However, the imaging methods of the present invention encompass any non-toxic imaging agent that is transported by the multidrug resistance transport system. Alternative preferred imaging agents include, but are not limited to, other hexakis (R-isonitrile) technetium (I) complexes. Other embodiments encompass analogous complexes of paramagnetic and susceptibility metals such as lipophilic cation complexes of Mn, Fe, Gd, Dys for use in magnetic resonance imaging in vivo and in vitro and labeled positron-emitting ligands useful in positron emission tomography ("PET" scan). Alternative embodiments encompass other gamma-emitting labels such as rhenium, indium, iodine, and copper.

One preferred embodiment relates to the source of the Tc isotope. The specific activity of the $^{99m}$Tc-MIBI complex synthesized from $^{99m}$TcO$_4$⁻ obtained directly from commercial molybdenum/technetium generators, is extremely high. For example, in various embodiments disclosed herein, $^{99m}$Tc-MIBI was generally synthesized at $1-6 \times 10^8$ Ci/mole. By comparison, [$^3$H] TPP+, another lipophilic cation, is commonly supplied commercially at 5-100 Ci/mole. This provides an opportunity to decrease the molar concentration of cation accumulation by the biological preparation, yet remain within detectable limits. Since rhodamine 123 and TPP+ have been reported to have toxic effects on mitochondrial function at typical loading activities, the high specific activity and therefore low concentrations of $^{99m}$Tc-MIBI required for biological experiments minimize toxic side effects during physiological experimentation and diagnostic clinical imaging with the enhancement process.

Typical reversing agents include verapamil and quinidine. However, the invention can be practiced with any agent that reverses the multidrug resistance phenotype. Examples of alternative reversing agents include, but are not limited to vinblastine, vincristine, adriamycin, colchicine, daunomycin, dactinomycin, vanadate, cyclosporine and tetraphenylborate.

In one in vivo embodiment of the invention, a patient receives the detection agent in both the presence and absence of a reversing agent. The treatment is in either order. If the two drugs are first administered together, then following the detection process, the reversing agent is given sufficient time to leave the system before the administration of the agent alone. Following the treatments and detection, the measurements of accumulation of the agent in both cases are compared. Multidrug resistance tissue is detected in the presence of a reversing agent but not in its absence. Using this method, multidrug resistant tissue is located without invasive procedures.

One of the most formidable obstacles to successful chemotherapeutic treatment of tumors is the acquisition by tumors of the multidrug resistance phenotype. Presently, the acquisition of multidrug resistance is usually discovered when the patient no longer responds to the prescribed chemotherapeutic regimen.

In vivo evaluation of the multidrug resistance phenotype is highly desirable. If it is necessary to ascertain the presence of drug-resistant tumor cells in a cancer patient with solid tumors, either prior to or during treatment, doing so without surgery is much preferred. However, the location of an multidrug resistance tumor may not be known, so surgery would be complicated or precluded. Moreover, the presence of multiple metastases or of masses that impinge on an organ may preclude surgery as an alternative.

Whole body imaging in patients with tumors has previously demonstrated uptake of $^{99m}$Tc-MIBI within mediastinal and pulmonary metastasis from thyroid cancer (Muller, S. T., et al., *J. Nucl. Med.* 28:562 (abstract) (1987)), untreated malignant lung lesions (Hassan, I. M. et al., *Clin. Nucl. Med.* 14:333 (1989) and known bronchial carcinomas (Muller, S. T. et al., *J. Nucl. Med.* 30:845 (abstract) (1989)).

Accordingly, in a highly preferred method of the present invention, multidrug-resistant tumors are detected in cancer patients without the need for surgery by administering to cancer patients an imaging agent of the present invention in the presence and absence of a reversing agent and comparing the images.

In alternative methods of the present invention, agents are not detected by imaging but by quantitative measurement of the intracellular accumulation (e.g., in a gamma counter or as by scanning radiograms by densitometry).

In a highly preferred embodiment of the methods of the present invention the imaging agent is $^{99m}$Tc-MIBI. The presence or absence of expression of the multidrug resistance phenotype in tumors is evaluated non-invasively by the scintigraphic imaging with $^{99m}$Tc-MIBI of cancer patients before and after the administration of a reversing agent. Those tumors significantly expressing the multidrug resistance phenotype will show little $^{99m}$Tc-MIBI localization in the absence of the reversing agent but enhanced uptake of $^{99m}$Tc-MIBI within the tumor or metastasis during infusion of the reversing agent. Those tumors not expressing the multidrug resistance P-glycoprotein should show $^{99m}$Tc-MIBI localization initially, but should not demonstrate reversing agent-induced enhancement of net uptake. $^{99m}$Tc-MIBI is a preferred imaging agent for whole tissue imaging. Alternative imaging agents include, but are not limited to the agents mentioned above. A highly preferred combination is $^{99m}$Tc-MIBI as the imaging agent and verapamil, quinidine, or cyclosporine as the reversing agent. However, the invention can be practiced with any agent that reverses the multidrug resistance phenotype. Examples of alternative reversing agents are discussed above.

The methods of the present invention are also applicable to whole tissue and cells in vitro. The invention is advantageous over current methods of determining the multidrug resistance phenotype in vitro because it is rapid and simple. Using presently available methods, before the multidrug resistance phenotype can be evaluated in whole tissue, a single cell suspension must be created (e.g., for flow cytometry) or even more laborious techniques must be used, such as momolayer cell culture. Using the method of the current invention, it is possible to detect the multidrug resistance phenotype in tissue without, or with minimum, disaggregation. Thus, therapeutic regimens may be decided with less delay than with presently available methods.

Current in vitro procedures for detecting the multidrug resistance phenotype involve forming either cell monolayers or single cell suspensions because the detectable emission (i.e., beta rays or fluorescence) does not penetrate and pass through intervening biological material. Thus, there is no rapid procedure for assaying the multidrug resistance phenotype of cells in a tissue or a cell mass, such as a tumor or tumor biopsy. Tissue would have to be dispersed into single cells for analysis and may have to be cultured. Cell culture, however is time consuming and also alters the selection pressures so that the cultured cells do not display the same phenotype or genotype as the cells in vivo. For example, the overexpression of the multidrug resistance gene in a tumor occurs as a result of the selection and multiplication of single or a few mutant cells as the tumor is subjected to a chemotherapeutic drug. If the tumor is excised and grown in tissue culture, the genotype may change because the selection pressure is not the same. This may interfere with the proper analysis of the tumor and hence with prescription of a effective therapeutic regimen. With the methods of the present invention, however, the tumor could be analyzed without dispersion and growth in culture. Relevant prescription would then be more likely.

Further, tumors are usually genotypically and phenotypically heterogeneous. New genotypes may arise in a very small or minute portions of a tumor and may not be detectable by routine methods. For example, the multidrug resistance phenotype occurring in a small area of a tumor, may be missed if the tumor cells are dispersed or merely biopsied. With the methods of the present invention, since a small area would be intact, imaging the tumor would reveal such small pockets of multidrug resistant cells.

Accordingly, the invention embodies methods of assaying the multidrug resistance phenotype in whole tissue or tissue biopsies by incubating the tissue or biopsy with the agents of the present invention. In a preferred embodiment, the tissue is exposed to the agent in the presence and absence of a reversing agent, such as those mentioned above. Accumulation of the agent in the tissue is measured in both cases and the measurements are compared. In alternative embodiments, the agent is administered alone and the measurement obtained is compared with the measurement obtained with normal control tissue. In one preferred embodiment, the agent is an imaging agent. $^{99m}$Tc-MIBI is a preferred imaging agent for whole tissue imaging. Alternative imaging agents include, but are not limited to the agents mentioned above. A highly preferred combination is $^{99m}$Tc-MIBI as the imaging agent and verapamil or quinidine as the reversing agent.

The invention also embodies methods of designing chemotherapy regimens by assaying the multidrug resistance phenotype in patients or their explanted tissue either prior to or during treatment. During the course of chemotherapy, when it is determined that a multidrug resistance-negative tumor (previously showing agent localization) converts or recurs with multidrug resistance (expressed as loss of agent localization), this valuable information is used to guide therapeutic management of the patients. Accordingly, in an embodiment of the invention, patients are evaluated for the multidrug resistance phenotype prior to initiation or continuation of chemotherapy. Those patients deemed phenotypically multidrug resistance-positive are spared the toxic and debilitating side effects of futile chemotherapy and alternative regiments or treatment ought.

With the method of the present invention, it is also possible to evaluate in vivo the efficacy of alternative chemotherapeutic drugs. In one embodiment of the invention, the ability of a drug to act as a chemosensitizer (reversing agent used in chemotherapy to facilitate the uptake of a chemotherapeutic drug in drug-resistant tumor cells) is determined. An agent of the present invention and a potential chemosensitizer are administered to a patient. If the drug is able to reverse the multidrug resistance phenotype, the agent will be retained in the patient's tumor cells in the presence of that drug but not in its absence. The chemosensitizer is then used to facilitate the administration of or to test the efficacy of anti-tumor drugs.

Further, the location of tumors not detectable by standard means (e.g., CAT scan) is determinable if these tumors have the multidrug resistance phenotype. Thus, the methods of the present invention provide means to monitor progression or regression of the disease during chemotherapy.

The discovery of the present invention also provides embodiments in which agents are transported by other members of the ATP binding cassette transport family of proteins. For example, one embodiment of the invention is a test for sensitivity to new anti-malarial agents in drug-resistant malaria parasites in which the pfMDR gene is over-expressed or a test of bacterial transport function where the transporter belongs to the family.

The invention may also be extended to imaging those tissues that naturally express elevated levels of the multidrug-resistance transport protein relative to other normal tissues. This includes liver, bone marrow, adrenals, kidney, and lung. These tissues would appears as photodeficient areas.

II. Therapeutic Methods and Compounds

Based on the discovery that Tc-MIBI is transported out of cells by the multidrug resistance transport system, the present invention relates to design and therapeutic uses of similar complexes that bind to the multidrug resistance transporter protein. The invention thus provides a new class of reversing agents and direct chemotherapeutic compounds. The present invention is therefore generally directed to a method for directly killing a cell or reversing the multidrug resistance phenotype in a multidrug resistant cell comprising administering the complexes of the present invention to the cell.

Accordingly, the invention is directed to a method of enhancing the intracellular accumulation of a drug in multidrug resistant cells wherein the accumulation is dependent upon transport by the multidrug resistant transport system which involves P-glycoprotein. In such methods, the compound of the present invention is co-administered with the drug.

The administration may be in vitro or in vivo. In preferred embodiments of the invention the enhancement of accumulation of the drug is in multidrug resistant cells in vivo. In preferred embodiments of the invention the complexes are administered to cancer patients in vivo as a means of treating tumors which have become multidrug resistant in the course of therapy.

Accordingly, chemotherapeutic agents are administered with the compounds of the present invention. The coadministration is designed to enhance accumulation of the agent following reversal of the multidrug resistance phenotype by interaction of the compounds of the present invention with the multidrug transport system. Thus, the coadministration is designed to cause the chemotherapeutic agent to accumulate in amounts effective for cytotoxicity whereas when the agent is administered alone, accumulation in effective amounts does not occur. This coadministration regimen can be applied to any cell which exhibits the multidrug resistant phenotype as a result of overexpression of the multidrug resistance protein, e.g., P-glycoprotein.

The compounds of the present invention also provide methods to study cytotoxicity in vitro in a search for new cytotoxic compounds. Thus, multidrug resistant cells may be exposed in vitro to the potential compound in the presence of the compounds of the present invention. This regimen also allows determination of effective combinations for chemotherapy by demonstrating which chemotherapeutic drugs can be effectively accumulated in multidrug resistant cells as a result of the addition of the compounds of the present invention. These regimens may be used in tissue biopsies to assess effective cytotoxic agents for a particular patient. Accordingly, the compounds of the present invention may be used to tailor chemotherapy to the individual patient by assessing the effect in biopsies of combinations of the compounds of the present invention and various known or potential chemotherapeutic agents.

In other embodiments of the invention, the present invention is directed to a method of enhancing the effect of a reversing agent. In these embodiments, the compounds of the present invention are added to a regimen which already includes the use of a reversing agent being co-administered with a chemotherapeutic agent or other agent whose intracellular accumulation in multidrug resistant cells is desired. Thus, the compounds of the present invention would be administered concurrently with another known reversal agent to enhance the cytotoxicity or reversing properties of the second agent.

In further embodiments of the invention, the invention is directed to the use of the compounds of the present invention alone as a method of killing multidrug resistant cells in vivo and in vitro. This encompasses direct use of radioactive isotopes incorporated into the metal core of the metal isonitrile complexes for local deposition of ionizing radiation into the multidrug resistant cells. In preferred embodiments, the multidrug resistant cells are found in tumors in patients in vivo. Radioactive ligands could also be synthesized and bound to the core metal for use as selective radioactive agents for such radiotherapy. In addition, in other embodiments of the invention, radio frequency energy applied at the nuclear magnetic residence frequency of the metal core of the agent could be used therapeutically to selectively deposit thermal energy in multidrug resistant cells, particularly tumors, while patients are inside a nuclear magnetic residence imaging device.

In alternative embodiments of the invention, the method would be directed to the use of the compounds of the present invention as enhancing agents to increase tissue accumulation of $^{99m}$Tc-MIBI or other technetium isonitrile complexes during diagnostic imaging of tissue perfusion or tumors using gamma camera scintigraphy. In this case, the complexes of the present invention would serve as the reversing agent relevant to the diagnostic use of the isonitrile complexes discussed in the section above headed "Diagnostic Imaging."

In further embodiments of the invention, the complexes of the present invention may function as novel antimalarial drugs. This is because the transport system which transports drugs in protozoans involves an ATP-binding transport system similar to the P-glycoprotein multidrug resistant transport system.

The complexes of the present invention could also be used as antibiotics by inhibiting bacterial membrane transport systems, which systems operate through ATP-depending binding proteins homologous to the P-glycoprotein multidrug resistant transport system. The compounds and methods of the present invention could be applied to any of the transport systems which function through transport proteins with amino acid similarities and structural relationships with the multidrug resistant transport protein, P-glycoprotein. Many of these proteins have been discussed in the background section above.

In embodiments of the therapeutic aspect of the invention, typical structures are hexakis isonitrile complexes of a core metal which may be, but is not limited to, rhenium or technetium. Other multi-ligand isonitrile complexes of iron, cobalt, manganese, nickel, chromium and copper can be synthesized. In these embodiments, all metals but technetium have stable (non-radioactive) isotopes found in nature and which are suitable for drug manufacture.

In alternative embodiments of the invention, radioactive isotopes of all the metals may be synthesized for use during drug design, for example, for performing biodistributions or for therapeutic exploitation of the radioactive emissions into cancer tissues. The side groups of these compounds are substituted alkyl and aryl isonitrile ligands.

Preferred compounds of the present invention include but are not limited to hexakis (arylisonitrile (rhenium) (I) complexes as drugs for the methods of the present invention. Preferred embodiments include hexakis arylisonitrile rhenium I complexes where the arylisonitrile ligand is optimized for binding affinity to the multidrug resistant transport protein. In a particularly preferred embodiment the ligand is trimethoxy-phenylisonitrile (see FIG. 7).

In preferred embodiments of the invention, ligands are analogous to the substituted aryl structure of verapamil, a known high affinity P-glycoprotein binding drug and reversing agent. In alternative embodiments of this therapeutic aspect of the invention, in addition to the core metal, the aryl group may be based on any of the other reversing compounds known to bind to P-glycoprotein. Structures may also be based on compounds which bind to vesicles produced from multidrug resistant cell membranes, particularly compounds which may interfere with the labeling of such vesicles or P-glycoprotein directly.

Preferred isonitrile ligands include, but are not limited to, 4-methoxyphenylisonitrile; 3-,4-dimethoxyphenylisonitrile; 3-,5-dimethoxyphenylisonitrile; 3-,4-,5-trimethoxyphenylisonitrile; 4-methoxybenzylisonitrile; 3-,4-dimethoxybenzylisonitrile; 3-,4-,5-trimethoxybenzylisonitrile; 3-,4-dimethoxyphenethylisonitrile; 3-,4-,5-trimethoxyphenethylisonitrile; 4-methoxyphenethylisonitrile; phenylisocyanide isonitrile; phenylacetyl isonitrile; phenylacetamide isonitrile; or 3-,4-O-CH$_2$-O-phenylisonitrile. Each isonitrile ligand has been readily synthesized from the corresponding primary amine by standard reaction with chloroform and base in the presence of phase transfer catalyst (Nicolini, M. et al., Eds., "Technetium and Rhenium" in *Chemistry and Nuclear Medicine,* Cortina Internet, Verona Italy (1986). The hexakis Tc or Re complex of the isonitrile ligand can be synthesized by addition of pertechnetate or perrhenate (ReO$_4$—) and reducing agent (Na$_2$SO$_4$) to the free ligand as described (Piwnica-Worms et al., *Invest. Radiol.* 24:25 (1989)). Because most known reversal agents contain a substituted aryl function, in particular, di- or trimethoxy phenyl functions, rational design of optimal arylisonitrile ligands with high affinity for P-glycoprotein would likely arise within this class. In vitro cell binding assays with cells enriched in P-glycoprotein would be used to screen for optimal binding agents (see FIG. 10). Competition for photoaffinity labeling of membrane preparations from P-glycoprotein enriched cells could also serve to assay for an optimized structure of the ligand. Such an assay with hexakis (methoxyisobutylisonitrile) $^{99m}$Tc shown in FIG. 6. Because it is known to those skilled in the art that Tc-isonitrile complexes are chemically identical to Re-isonitrile complexes, all such assays performed with the readily available $^{99m}$Tc metal as the core of the complex are excellent predictors of the behavior of the non-radiolabeled Re complex (Nicolini, M. Bandoli, G. Mazzi, U. (Eds.), *Technetium and Rhenium in Chemistry and Nuclear Medicine,* Cortina International, Verona, Italy, (1986).

Assays for the efficacy of such compounds include, but are not limited to, the ability to enhance the uptake of a chemotherapeutic agent such as daunorubicin or vincristine, the ability to block the efflux of chemotherapeutic agents from cells, the ability to interfere with photoaffinity labeling of multidrug resistant membrane vesicles, and the general ability to compete with chemosensitizing agents in any of the assays involving reversal of the multidrug phenotype or binding to P-glycoprotein.

By the term "ATP-binding cassette transport protein" is intended, for the purpose of the present invention, a protein that is a member of the ATP-binding cassette superfamily of transport proteins. This family is recognized by sequence identity over a "cassette" of about 200 amino acids. This cassette is an ATP-binding domain which is the distinguishing feature of this family of transport proteins. These domains share about 30–40% sequence identity among the members of the superfamily. A putative member of the superfamily would be recognized by sequence comparison of the primary structure with a primary consensus sequence or individual sequences of these proteins using routine computerized sequence scanning methods. The degree of identity in the conserved domain between any pair of these proteins is essentially the same whichever two proteins are compared. It is important to emphasize that these ATP-binding proteins are distinct from other proteins that bind ATP in that the sequence homology is much greater than is required for merely nucleotide binding. That is, the homology extends considerably beyond the two consensus nucleotide-binding sequences of Walker et al. (*EMBO J.* 1:945 (1982)) which comprise five and nine amino acids.

The ordinary skilled artisan would recognize a putative member of this distinctive family by computerized alignment of the primary sequence with the primary sequence of one or more of the known ATP-binding cassette transport proteins. Computerized sequence comparison and alignment is done with any one of the well-known and routinely used sequence homology/identity scanning programs. These programs would be readily available to the skilled artisan. The putative member of the family should contain, in addition to the two short consensus nucleotide-binding sequences of Walker et al. (*EMBO J.* 1:945 (1982)) incorporated herein by reference), a region of homology surrounding the consensus sequences wherein the region of homology spans around 200 nucleotides and is approximately 30–40% homologous with a region in the known members of the family. To ensure identity, the skilled artisan would generally know to compare the novel sequence with several known members of the family (see, for example, Juranka et al. *FASEB J.* 3:2584 (1989); Gerlach et al. *Nature* 324:485 (1986); Chen et al. *Cell* 47: 381 (1986); Gros et al. *Cell* 47:371 (1986); Higgins et al. *BioEssays* 8:111 (1988); Kamijo et al. *J. Biol. Chem.* 265:4534 (1990); Higgins et al. *Nature* 323:448 (1986); Hyde et al. *Nature* 396:362 (1990) all herein incorporated by reference).

By the term "cell" is intended any one of the components that make up an organized tissue, consisting of a nucleus which is surrounded by cytoplasm which contains the various organelles and is enclosed in the cell or plasma membrane. For the purpose of the present invention, cells are in vivo as part of the living organism, in explanted tissue taken from a living organism, or in cell culture.

By the term "multidrug resistance" for the purpose of the present invention is intended the phenotype that occurs in a cell as the result of the overexpression of the gene product of the multidrug resistance gene or its homolog. By "multidrug resistance gene" is intended that DNA sequence which encodes P-glycoprotein and its functional equivalents and whose amplification confers upon a cell cross-resistance to toxic drugs. By "homolog" is intended the DNA sequence in another species, which sequence corresponds to the multidrug resistance gene.

By the term "administer" is intended any method for introducing the compositions of the present invention into a subject. Typical methods include, but are not limited to, oral, intranasal, parenteral (intravenous, intramuscular, or subcutaneous), or rectal. The term "administer" also relates to the application of substance ex vivo as in cell or organ culture.

When administration is for the purpose of treatment, administration may be for either prophylactic or therapeutic purposes. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

By the term "coadminister" is intended that each of at least two compounds be administered during a time frame wherein the respective periods of biological activity overlap. Thus the term includes sequential as well as coextensive administration of the compounds of the present invention.

By "compound" is intended a chemical entity, whether in the solid, liquid, or gaseous phase, which entity may be used on or administered to animals, including humans, as an aid in the diagnosis, treatment, or prevention of disease or other abnormal condition, for the relief of pain or suffering, or to control or improve any physiologic or pathologic condition. The term "compound" should be read to include synthetic compounds, natural products and macromolecular entities such as polypeptides, polynucleotides, or lipids and also small entities such as neurotransmitters, ligands, hormones or elemental compounds. The term "compound" is meant to refer to that compound whether it is in a crude mixture or purified and isolated.

By the term "transport" for the purpose of the present invention is intended the ATP-binding protein-dependent movement of a compound across the membrane of a living cell and especially where the protein is P-glycoprotein or its homologs. Transport may encompass mechanisms wherein a substrate is bound reversibly or irreversibly to the transport protein.

By "intervening" is intended, for the purpose of the present invention, the occurrence of biological tissue between the cell being detected and the detection device. The biological tissue of relevance is of a thickness such that it cannot be traversed by beta emission, fluorescence, or other clinical detection means such as heat (thermography) or spectrophotometry. Therefore, such means of detection are not useful for detection of multidrug-resistant cells or tissue in vivo, where the organs and other biological tissue in a living body interfere with or prevent detection. These means, similarly, are not useful for detecting multidrug-resistant cells enclosed in a cell mass such as a tissue biopsy or whole tumor.

By the term "imaging" for the purpose of the invention is intended the production in clarity, contrast, and detail in images, either by analogue or digital devices, especially in radiological images.

By the term "scintigraphy" is intended the production of two dimensional or three dimensional reconstructed images of the distribution of radioactivity in tissues after the internal administration of radionuclide, the images being obtained by a scintillation camera.

By the terms "chemosensitizer" or "reversing agent" are intended for the purpose of the present invention, a compound that allows the net accumulation of toxic compounds in multidrug-resistant cells equivalent to the net accumulation of said toxic compounds in non-multidrug-resistant cells. The presence of these agents may also merely increase the amount of the toxic compound able to accumulate in a multidrug resistance cell compared to the amount accumulated in the absence of the agent.

By the term "tumor" is intended for the purpose of the present invention, a new growth of tissue in which the multiplication of cells is uncontrolled and progressive. The tumor that is particularly relevant to the invention is the malignant tumor, one in which the primary tumor has the properties of invasion and metastasis and which shows a greater degree of anaplasia than do benign tumors.

By "R" is intended alkyl, substituted alkyl, aryl, or substituted aryl groups. R groups are found in the general formula $-CR_3$ where R can be identical or different and includes the elements H, C, N, O, S, F, Cl, Br, and I. Representative examples include, but are not limited to, $-CH_3$, $-CH_2CH_3$, $CH(CH_3)_2$, $-C(CH_3)_3$, $-C(CH_3)_2 OCH_3$, $-C(CH_3)_2 COOCH_3$, $-C(CH_3)_2 OCOCH_3$ $-C(CH_3) CONH_2$, $-C_6H_5$, $-CH_2(C_6H_4)OH$, or any of their isomeric forms having the general composition as the isonitrile radionuclide complexes in U.S. Pat. No. 4,452,774 which is incorporated herein by reference.

By "alkyl" is intended any straight, branched, saturated, unsaturated or cyclic $C_{1-20}$ alkyl group. Typical $C_1$–$C_{20}$ alkyl groups include, but are not limited to, methyl, ethyl, n-propyl, i-propyl, n-butyl, t-butyl, i-butyl, pentyl and hexyl groups. Preferred alkyl groups may include isopropyl, isobutyl, 2-ethyl-n-propyl, and t-butyl.

By "aryl" is intended any cyclic hydrocarbon based on a six-membered ring. Typical aryl groups include, but are not limited to, phenyl, naphthyl, benzyl, phenethyl, phenanthryl, and anthracyl groups. Preferred groups include, but are not limited to, methoxyphenyl; dimethoxyphenyl; trimethoxyphenyl; methyoxybenzyl; dimethoxybenzyl; trimethoxybenzyl; dimethoxyphenethyl; trimethoxyphenethyl; methoxyphenethyl; phenylisocyanide; phenylacetyl; phenylacetamide; or O—CH$_2$—O—phenyl.

By "substituted alkyl" and "substituted aryl" is intended any alkyl or aryl group in which at least one carbon atom is covalently bonded to any functional group comprising the atoms H, C, N, O, S, F, Cl, Br and I.

Typical substituted alkyl groups include but are not limited to amino, $C_{1-6}$ alkylamino, $C_{2-12}$ dialkylamino, $C_{1-6}$ alkoxy, and $C_{2-6}$ alkylcarboxy. Typical substituted aryl groups include, but are not limited to the above-listed aryl groups substituted by halo, hydroxy, $C_1$–$C_6$ alkoxy, amino, and the like.

By the term "animal" is intended any living creature that contains cells in which the intramembrane potential is reduced by the administration of agents of this invention. Foremost among such animals are humans; however, the invention is not intended to be so-limiting, it being within the contemplation of the present invention to apply the compositions of the invention to any and all animals which may experience the benefits of the application.

By the term "over-express" is intended for the purpose of the present invention, the production of an ATP-binding cassette transport protein in a cell type in amounts exceeding that normally produced in that cell type. Although expression may vary amongst normal cell types, within each type an ATP-binding cassette transport protein is expressed within a normal physiological range. Over-expression may be due to gene amplification, an increase in RNA transcription rates, increase in RNA stability, increase in mRNA translation, or any other molecular process which results in amounts of ATP-binding cassette transport protein exceeding those amounts found in normal cells. The normal range of expression in a given cell type can be determined by routine methods as by assaying the ATP-binding cassette transport protein, its mRNA, or its gene. Assays may be those commonly used in the art such as immunoassay, PAGE, western blot, Southern and northern blots, Cot analysis, Rot analysis, and competition hybridization procedures.

By "reversing the multidrug resistance phenotype", for the purposes of the present invention, is intended causing cells, which over express the multidrug resistance gene product and therefore survive in the presence of cytotoxic agents, to become sensitive to the agents. The agents may be chemotherapeutic agents or agents which are otherwise toxic to cells. The agents are transported by the multidrug transport protein. The reversal may occur by irreversibly binding to the transport protein thereby preventing the efflux of the therapeutic compound irreversibly or by competitively inhibiting said therapeutic compound by binding the sites in the transport system ordinarily occupied by that compound. Thus the reversal may be transient or permanent.

By "efflux" is intended the transport of a chemotherapeutic compound or other compound whose intracellular accumulation is desired, out of a cell.

By (R-isonitrile) metal complex is intended compounds comprising a core metal atom, either radioactive or non-radioactive, coordinate bonded to the terminal carbon of the R-isonitrile ligands described above.

Having now generally described the invention, the following examples illustrate the methods of the present invention.

EXAMPLES

EXAMPLE 1

Experimental Solutions

Control buffer was a modified Earle's balanced salt solution (MEBSS) with the following composition (nM): Na$^+$, 145; K$^+$, 5.4; Ca$^{2+}$, 1.2; Mg$^{2+}$, 0.8; Cl, 152; H$_2$PO$_4$, 0.8; SO$_4^{2-}$, 0.8; dextrose, 5.6; HEPES, 4.0; and bovine calf serum, 1% (v/v); pH 7.4±0.05; 37° C. Verapamil and quinidine were dissolved into DMSO prior to addition to buffer. DMSO alone has no significant effect on contractile activity, action potential configuration (Lieberman, M., et al., *Dev. Biol.* 31:380–403 (1973)) or Tc-MIBI uptake kinetics (Piwnica-Worms, D., et al., *Circ.* 82:1826–1838 (1990)).

Synthesis of the radiolabeled compound [$^{99m}$Tc]MIBI was performed using a one-step kit developed at DuPont Medical Products, Billerica, Mass. The kit reaction vial contains the isonitrile ligand in the form of tetrakis (2-methoxy isobutyl isonitrile) Copper (I) tetrafluoroborate (1.0 mg), a stannous chloride reducing agent (0.075 mg L-cysteine hydrochloride (1.0 mg), Sodium Citrate (2.6 mg) and mannitol (20 mg). The intrinsically radiolabeled complex was formed by adding [$^{99M}$Tc]TcO$_4^-$ (20–30 mCi, 2-25 pmol/mCi) in 1–2 ml saline (0.15M, NaCl), obtained from a commercial molybdenum/technetium generator (DuPont Medical Products, Billerica, Mass.), to the kit reaction vial, heating at 100° C. for 15 min, and allowing to cool to room temperature producing an almost quantitative yield of the [$^{99m}$Tc](MIBI)$_6^+$ complex. Excess reducing agent and starting materials were separated from the radiolabeled component as follows: the contents of the reaction vial were loaded via syringe onto a reversed phase Sep-Pak cartridge (C-18, Waters Assoc., Milford, Mass.) pre-wet with ethanol (3 ml, 90%) followed by distilled water (5 ml). Hydrophilic impurities were eluted from the cartridge by washing with saline (10 ml, 0.15M) and the desired $^{99m}$Tc-MIBI collected by elution with ethanol/saline (2ml; 9:1, v:v). Final total $^{99m}$Tc activity in the 2 ml effluent (stock) was assayed in a standard dose calibrator (CRC-12, Capintec, Ramsey, N.J.). Radiochemical purity was found to be greater than 97% by thin layer chromatography (aluminum oxide plates) using ethanol (absolute) as the mobile phase.

Statistics

Values are presented as mean ±SEM. Statistical significance was determined by the two-tailed unpaired Student's t test where indicated in the text (Wallenstein, S., et al., Circ. Res. 47:1-9 (1980)).

EXAMPLE 2

Tissue Culture of LZ, 77A and V79 Cells

LZ, 77A, and V79 cells were grown to confluence in approximately four days on 25 mm glass cover slips placed on the bottom of 100 mm plastic culture dishes in Minimal Essential Media (MEM) Alpha Medium supplemented with 10% fetal calf serum, 1% L-glutamine, and 1% penicillin/streptomycin solution at 37° C. in a 5% $CO_2$/95% air humidified environment. Serial passage was performed by gently shaking the cells off the culture dish during exposure to 0.25% trypsin solution for 2-3 minutes (room temperature) and diluting the cell suspension in growth medium 1:4 for LZ cells and 1:20-40 for 77A and V79 cells. For 77A and LZ cells, growth medium was also supplemented with 0.1 and 4 µg/ml adriamycin, respectively.

EXAMPLE 3

Radiotracer Uptake Methods

Radioactive uptake methods have been described in detail (Piwnica-Worms, D., et al., Circ. 82:1826=1838 (1990)). Briefly, coverslips with confluent cells were removed from culture media and pre-equilibrated for 40-60 seconds in MEBSS buffer. Uptake and retention experiments were initiated by immersion of coverslips in 60 mm glass Pyrex dishes containing loading solution consisting of buffer with 0.1-0.6 nM [$^{99m}$Tc-MIBI] (0.01-0.4 Ci/nmole; 25-100 uCi/ml). Preparations were removed at various times and rinsed three times in separate 25 ml volumes of ice-cold (2° C.) isotope-free buffer for 8 seconds each to clear extracellular spaces. For washout experiments, preparations were incubated in loading solution for 15 minutes, rinsed as above in ice-cold buffer, and then immersed in 30 ml of isotope-free MEBSS (37° C.) for the times indicated. Cell-associated activity was then determined. Preparations and aliquots of the loading buffer and stock solutions were counted in a well-type sodium iodide gamma counter after which cell protein on each coverslip was extracted in 1% sodium dodecylsulfate with 10 mM sodium borate and assayed by the method of Lowry (Lowry, O. H., et al., J. Biol. Chem. 193:265-275 (1951)). $^{99m}$Tc-MIBI binding to glass coverslips without cells was used as an estimate of non-specific adhesion to the substrate (<% of total activity obtained with cellular preparations); this value was subtracted from total uptake determinations to derive the cell-associated counts. Use of generator equilibrium equations (Lamson, M. L., et al., J. Nucl. Med. 16:639-641 (1975)) allowed calculation of absolute moles of Tc-MIBI in solutions and preparations. Results were therefore expressed as fmol cellular Tc-MIBI/mg protein per nM extracellular Tc-MIBI concentration.

EXAMPLE 4

Net accumulation of Tc-MIBI in LZ cells, a cell line highly selected for multidrug resistance phenotype, is only 0.3 fmoles Tc-MIBI/mg protein per nmolar extracellular Tc-MIBI (FIG. 1). This value is lower than that expected by simple equilibration of the agent into the cytosolic water space (approx. 5 fmoles/mg protein per $nM_o$) and implies active extrusion of Tc-MIBI by the multidrug resistance P-glycoprotein. High inhibitory doses of verapamil (1 mM) increases net accumulation of Tc-MIBI greater than 100-fold over net uptake in the absence of the inhibitor. V79 cells, a cell line which modestly expresses multidrug resistance P-glycoprotein, demonstrates control accumulation of Tc-MIBI to plateau levels 20-fold higher than LZ cells (FIG. 1). This is consistent with expectations for a cellular phenotype with a less robust efflux pathway for Tc-MIBI.

EXAMPLE 5

Figure 2:
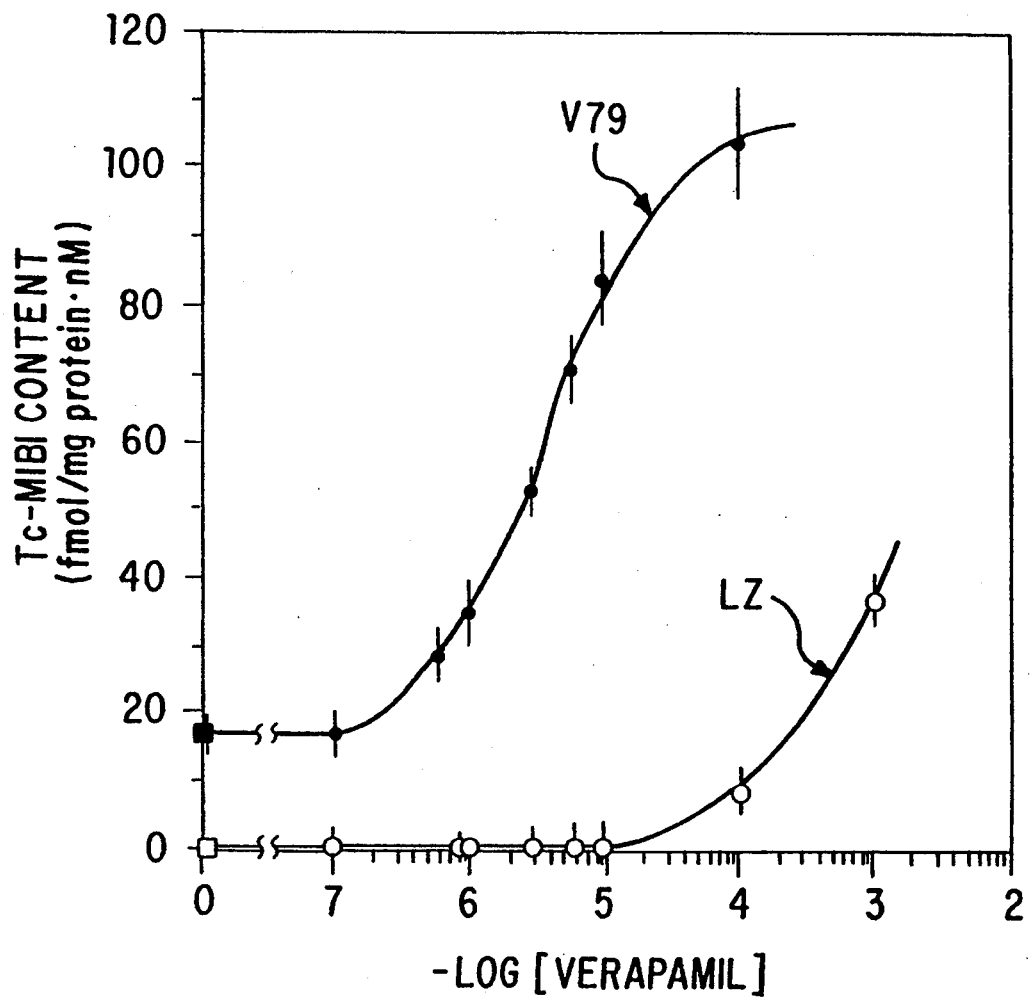
FIG. 2. Concentration-effect curve for verapamil enhancement of Tc-MIBI accumulation in LZ (□,○) and V79(■,●) cells. Preparations were incubated for 15 minutes in MEBSS containing $^{99m}$Tc-MIBI in the absence (□, ■) or presence (○, ●) of verapamil at the indicated concentrations and then cell associated activity determined. Points represent the mean ±SEM of 3-4 determinations each.

Verapamil, a known inhibitor of multidrug resistance P-glycoprotein (Gottesman, M. M. et al., J. Biol. Chem. 263:12163 (1990)), increases net accumulation of Tc-MIBI in LZ cells to the higher levels expected for potential dependent uptake of the agent (FIG. 2). Verapamil also enhances the net accumulation of Tc-MIBI in V79 cells causing an 6-fold increase in net Tc-MIBI accumulation (FIG. 2).

EXAMPLE 6

Figure 3:
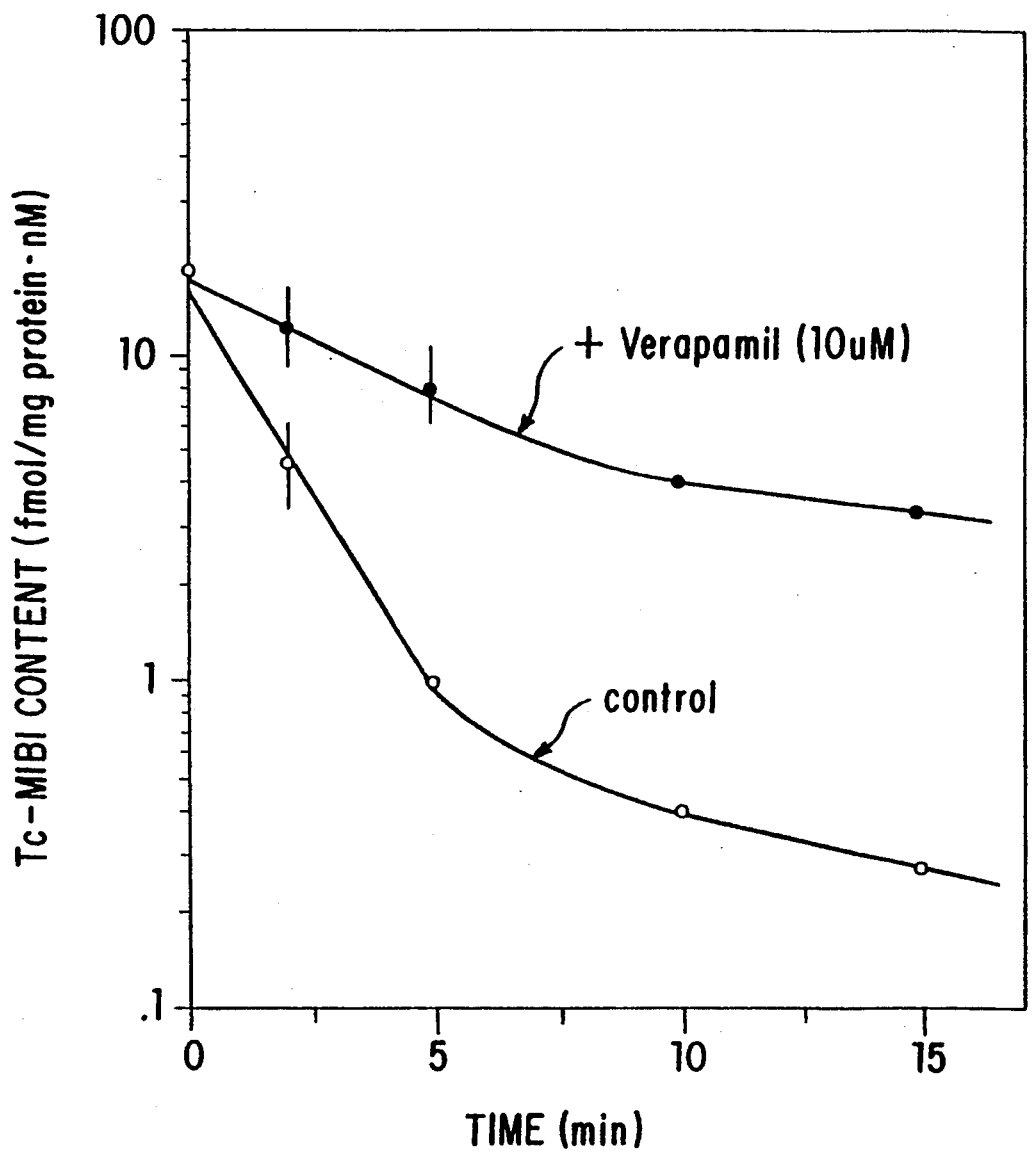
FIG. 3. Inhibition of Tc-MIBI efflux from V79 cells by verapamil. Cells were incubated in MEBSS containing $^{99m}$Tc-MIBI for 15 minutes (plateau loading), then transferred to $^{99m}$Tc-MIBI-free MEBSS washout buffer for various times in the absence (○) or presence (●) or verapamil (10 μm). Cell associated tracer activity was determined and expressed as fmol cellular Tc-MIBI/mg protein per nmolar Tc-MIBI concentration in the uptake buffer. Each point represents the mean of 4 determinations. Error bars represent ±SEM when larger than symbol. Note semilog plot.

Verapamil (10 uM) is shown to directly inhibit unidirectional efflux of Tc-MIBI from V79 cells (FIG. 3).

EXAMPLE 7

Figure 4:
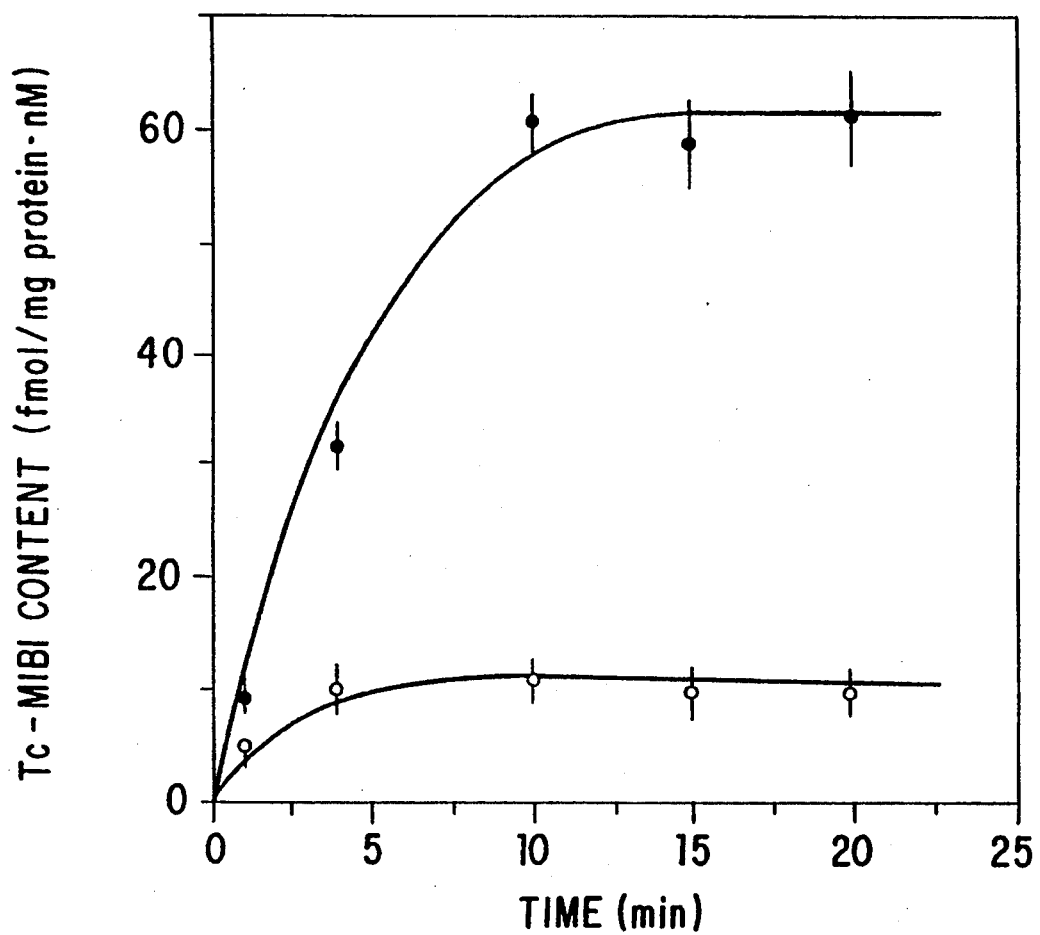
FIG. 4. Effect of quinidine on accumulation of Tc-MIBI in V79 cells. Cells were incubated for various times in MEBSS containing $^{99m}$Tc-MIBI in the absence (○) presence (●) of quinidine (10 uM) and then cell 1 associated activity determined. Points represent the mean ±SEM of three determinants each.

Quinidine, another drug known to inhibit the multidrug resistance P-glycoprotein, also increase net accumulation of Tc-MIBI in V79 cells (FIG. 4).

EXAMPLE 8

Figure 5A:
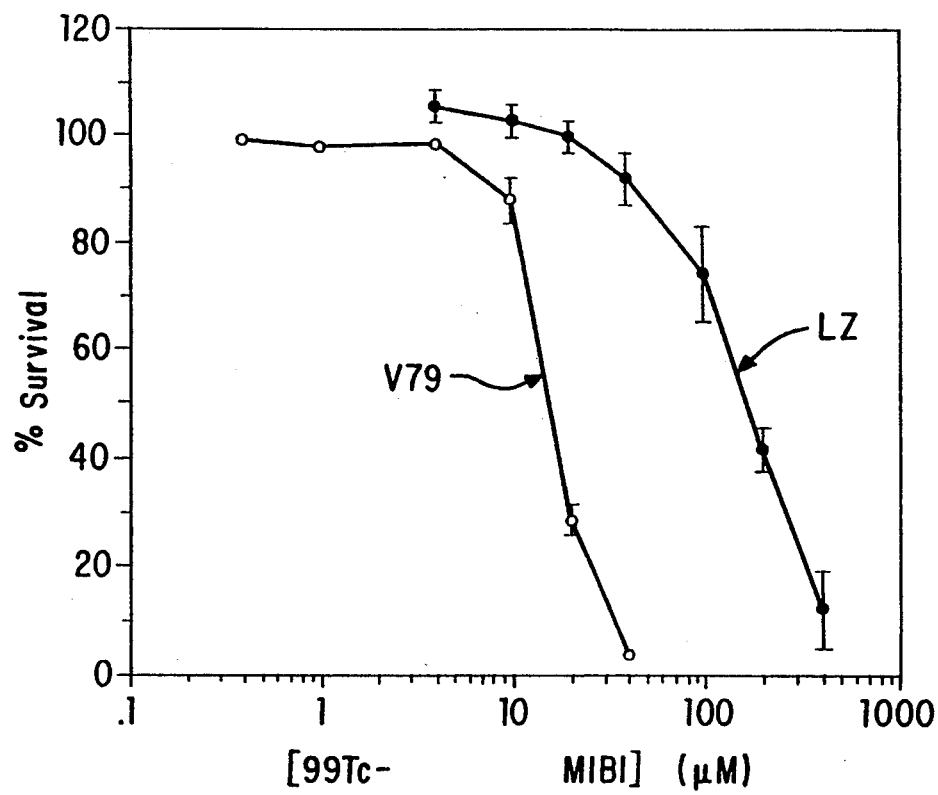
FIG. 5. Cell survival studies and LD$_{50}$ determination showing cytotoxicity of a $^{99}$Tc-isonitrile complex that is transported by the P-glycoprotein in vitro. Survival of parental V79 and multidrug resistant LZ cells (A) and parental Alex and multidrug resistant Alex/A.5 cells (B) in increasing concentrations of carrier-added $^{99}$Tc-MIBI. Methods: Cell survival assays were performed by plating 4,000–20,000 cells per well in 96 well microtiter plates in triplicate in three separate experiments. V79 and LZ cells were grown essentially as described in Example 2 while Alex and Alex/A.5 were grown as described by Goldstein, L., et al., *J. Natl. Cancer Inst.* 81:116 (1989). Multidrug resistant cells were cultured in drug free media for 72–96 hours prior to culture in $^{99}$Tc-MIBI. Surviving cells were assayed by staining with sulforhodamine B (Mazzanti, R., et al., *J. Cell Pharmacol.* 1:50 (1990)) at 72 hours for V79 and LZ cells or 96 hours for Alex and Alex A.5 cells. Survival was expressed as the percentage of surviving cells relative to growth in alpha-MEM media without $^{99}$Tc-MIBI. Standard error bars are displayed. LD$_{50}$ determinations were obtained by interpolation from the cell survival curves.
Figure 5B:
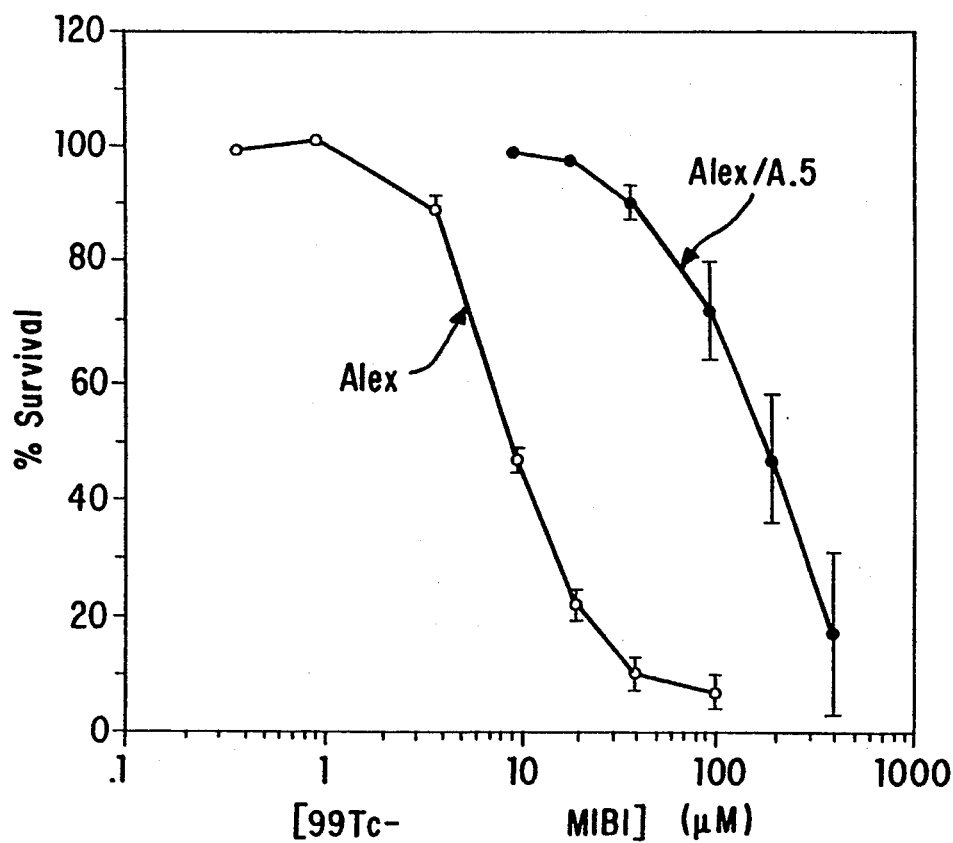

Micromolar concentrations of carrier-added 99Tc-MIBI is shown to be cytotoxic in hamster lung fibroblast cells (A) and human carcinoma cells (B) (FIG. 5). Note that Tc-MIBI, which is transported out of cells by P-glycoprotein, shows greater cytotoxic activity in drug-sensitive V79 and Alex cells compared to their multidrug-resistant derivative (LZ and Alex/A.5, respectively). As shown in the figure, $^{99}$Tc-MIBI was 11-fold and 13-fold more toxic in drug-sensitive V79 and human Alexander cells compared to their multidrug-resistant derivatives, respectively.

EXAMPLE 9

Figure 6A:
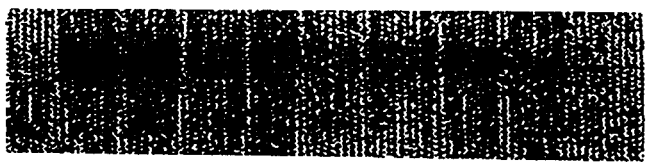
FIG. 6. Direct examination of the interaction of $^{99}$Tc-MIBI with MDR P-glycoprotein using the photoaffinity probe $^{125}$I-iodoaryl-azidoprazosin (IAP) showing inhibition by $^{99}$Tc-MIBI of IAP binding to P-glycoprotein. (A) Lane 1, V79, and lane 2, LZ, membranes photoaffinity labeled with IAP alone. P-glycoprotein labeling at 170 kDa is identified with arrow. LZ membranes labeled with IAP in the presence of 0.25, 2.5, 25, and 250 uM carrier-added $^{99}$Tc-MIBI (lanes 3–6) or verapamil (lanes 7–10), respectively. (B) Lane 1, CEM, and lane 2, CEM/VBL, membranes labeled with IAP alone (170 kDa, arrow). CEM/VBL membranes labeled with IAP in the presence of 0.25, 2.5, 25, 250 uM carrier-added $^{99}$Tc-MIBI (lanes 3–6) or verapamil (lanes 7–10), respectively. Methods: plasma membrane-enriched fractions from parental and multidrug resistant tissue cultured cells were isolated with a high speed spin (100,000×g) after dounce homogenization in 10 mM HEPES buffered 0.25M sucrose (pH 7.3) and removal of nuclei with a low speed spin (600×g). Fifty ug of membranes in a final volume of 50 ul were incubated with 2.5 nM $^{125}$I-iodoaryl azidoprazosin for 60 min at 25° C. in the dark (Greenberger, L., et al., *J. Biol. Chem.* 265:4394 (1990)). $^{99}$Tc-MIBI or verapamil were included at the concentrations indicated above. The sample was irradiated with an UV lamp (UVP, model UVL-56, 366 nm wavelength) for 20 min at 25° C. and fractionated on a 10% polyacrylamide gel. The gel was fixed with 10% acetic acid, rinsed in 2% glycerol, dried and exposed to XAR-5 film with an intensifying screen at 70° C. for 12–48 hrs.
Figure 6B:
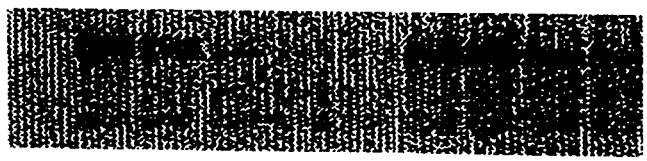
Figure 7A:
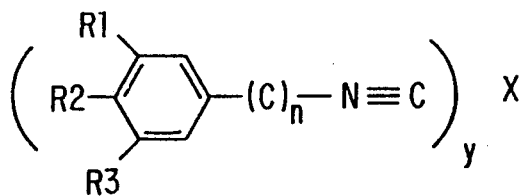
FIG. 7. Substituted arylisonitrile metal complexes and preferred ligands of rhenium hexakis arylisonitrile complexes as MDR P-glycoprotein binding (reversal) agents.
Figure 7B:
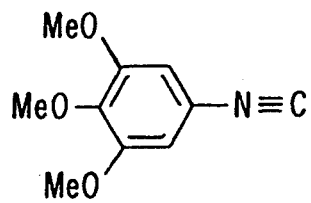
Figure 7B:
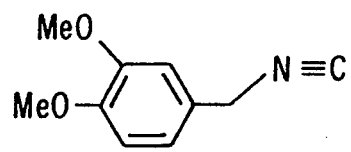
Figure 7B:
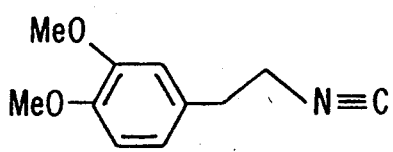
Figure 7B:
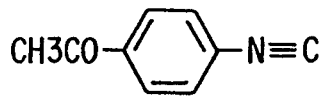
Figure 7B:
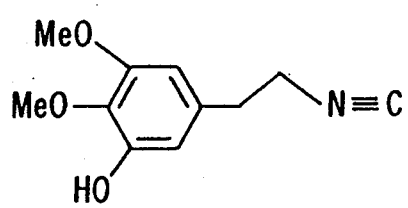
Figure 7B:
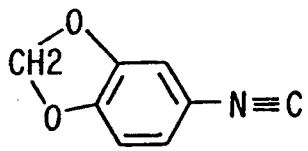

Inhibition by Tc-MIBI of photoaffinity labeling of P-glycoprotein with iodoaryl-azidoprazosin (FIG. 6). Note that Tc-MIBI half-maximally inhibited photolabeling of P-glycoprotein at between 100- and 1,000-fold molar excess (lanes 3-6), comparable to values for the known reversal agent verapamil (lanes 7-8).

EXAMPLE 10

Figure 8:
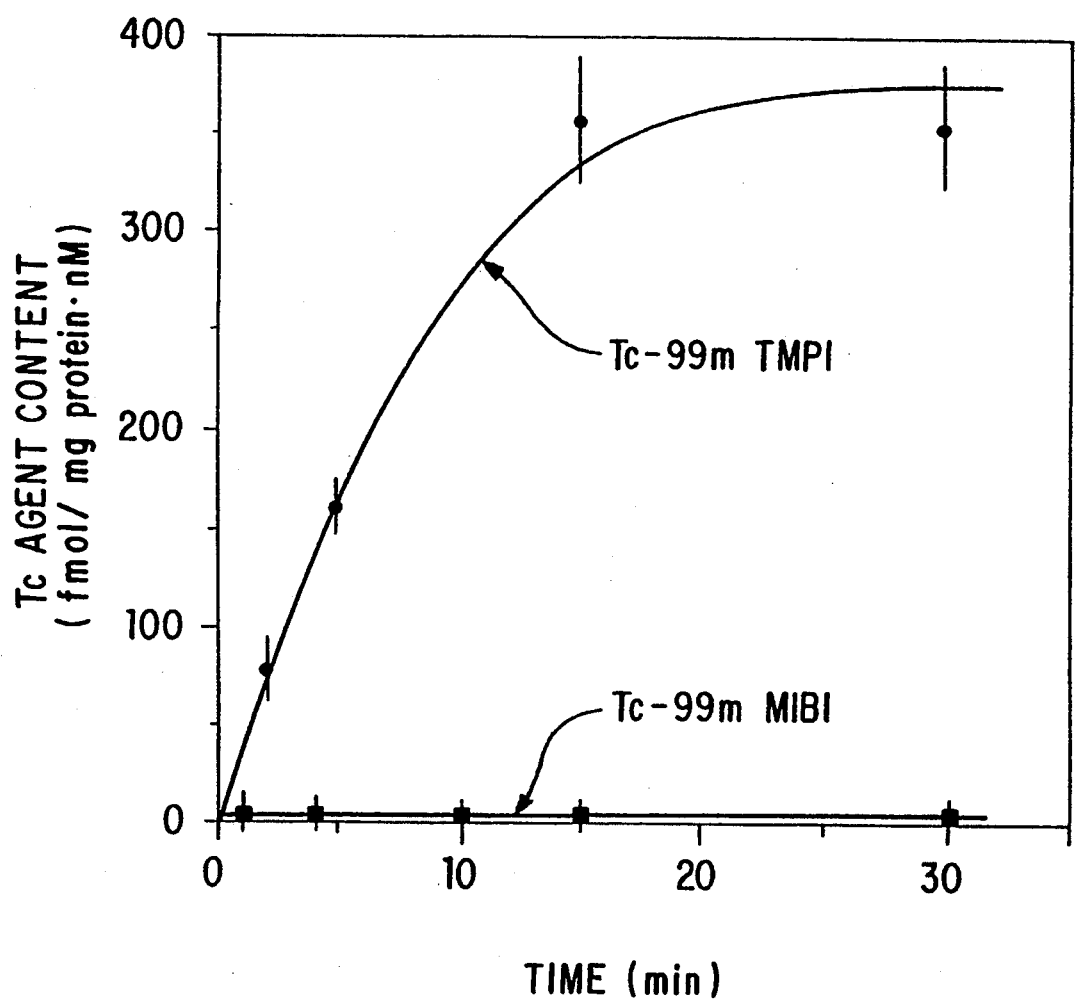
FIG. 8. Net accumulation of a novel Tc-isonitrile complex, Tc-TMPI (trimethoxyphenyl isonitrile) (●), compared to the P-glycoprotein transport substrate Tc-MIBI (■) in drug resistant 77A cells, a mammalian cell line expressing intermediately high levels of P-glycoprotein. Cells were plated in 100-mm petri dishes containing seven 25-mm glass coverslips on the bottom and grown to confluence in alpha-MEM medium (GIBCO) supplemented with L-glutamine (1%), penicillin/streptomycin (1%) and fetal calf serum (10%) in the presence of 0.1 ug/ml adriamycin. Synthesis of the radiolabeled compound $^{99m}$Tc-MIBI (hexakis (2-methoxyisobutylisonitrile)Tc) from a one-step kit formulation (Dupont Medical Products, Billerica, Mass.) and chromatographic analysis of radiochemical purity have been described (Piwnica-Worms et al., *Circulation* 82:1826 (1990)). The novel TMPI ligand was synthesized from the corresponding primary amine (trimethoxyphenylamine, Aldrich Chemical Co.) by standard reaction with chloroform and base in the presence of phase transfer catalyst as described by Kronauge, J. F. et al., *Inorg. Chem.* 30:4265 (1991) or Ugi, I., et al., *Angew. Chem., Int. Ed. Engl.* 4:472 (1965). The hexakis Tc-99m complex of TMPI was synthesized by addition of $^{99m}$TcO$_4^-$ and reducing agent (Na$_2$S$_2$O$_4$) to the free ligand as previously described (Piwnica-Worms et al., *Invest. Radiol.* 24:25 (1989)). Tracer accumulation was determined at the times indicated in cells incubated in modified Earle's balanced salt solution containing 145 mM Na$^+$, 5.4 mM K$^+$, 1.2 mM Ca$^{2+}$, 0.8 mM Mg$^{2+}$, 152 mm Cl$^-$, 0.8 mm H$_2$PO$_4^-$, 0.8 mM SO$_4^{2-}$, 5.6 mM dextrose, 4.0 mM HEPES (pH 7.4; 37° C.), 1% bovine calf serum, and 0.1–0.6 nM $^{99m}$Tc-isonitrile complex (25–100 uCi/ml; 0.1–0.4 Ci/nmole). Net accumulation of the $^{99m}$Tc-isonitrile complexes in each preparation was normalized to cell protein determined by the method of Lowry and to extracellular tracer concentration determined from an aliquot of the load solution using a well-type gamma counter (Piwnica-Worms et al., *Circ.* 82:1826 (1990)). Each point is the mean of 3–4 determinations; SEM did not exceed 15% of mean values.

In drug resistant 77A cells, a mammalian cell line expressing intermediately high levels of multidrug resistance P-glycoprotein, the net accumulation of the novel complex Tc-TMPI is compared with the net accumulation of Tc-MIBI (FIG. 8). Note that steady-state levels of Tc-TMPI content are 100-fold higher than Tc-MIBI. This is consistent with binding of Tc-TMPI to P-glycoprotein in these P-glycoprotein-enriched cells. Tc-MIBI has been previously shown to be an efflux transport substrate recognized by P-glycoprotein thereby resulting in low net accumulation. (FIG. 1).

EXAMPLE 11

Figure 9:
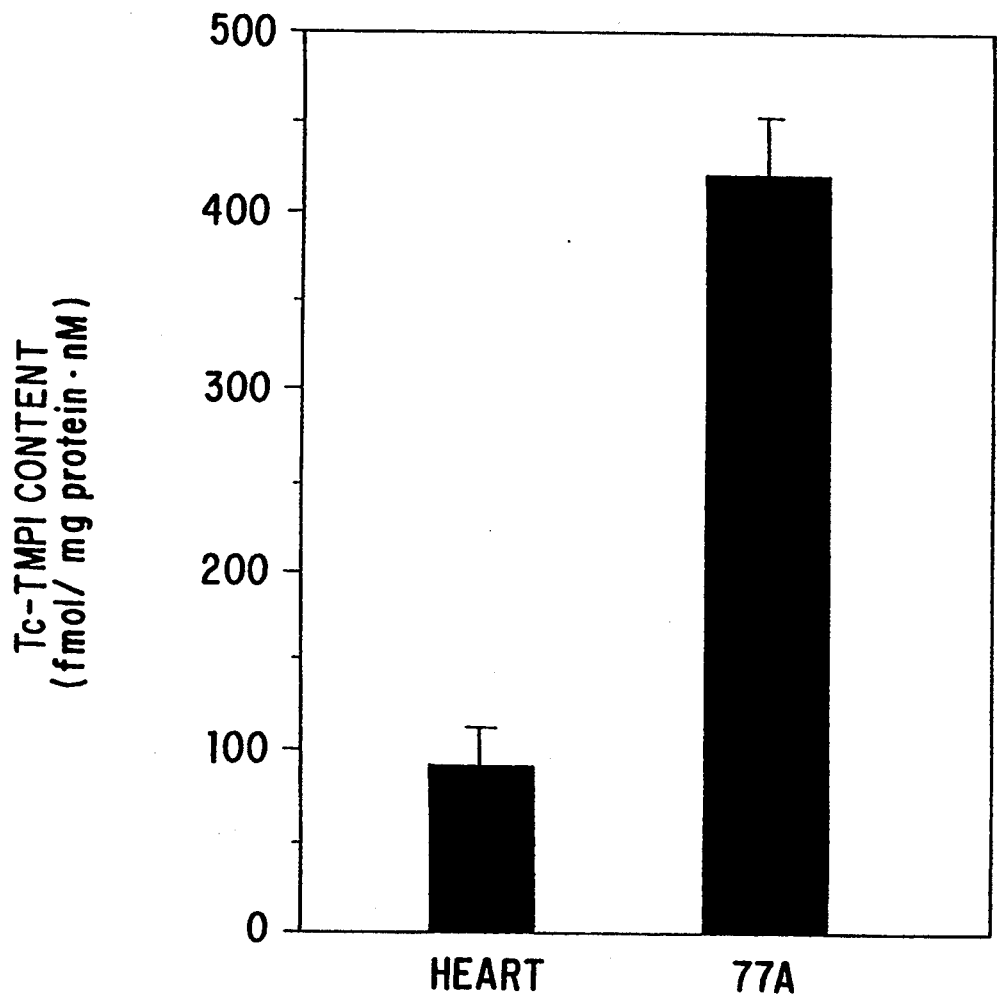
FIG. 9. Net accumulation at 60 minutes of the hexakis complex Tc-TMPI in cultured heart and 77A cells. Methods are the same as described in FIG. 8. Piwnica-Worms et al., (*Circ.* 82:1826 (1990)) also describes methods for obtaining primary cultured avian heart cells.
Figure 10A:
FIG. 10. Scintigraphic images of the novel hexakis complex Tc-TMPI binding in vivo in adult rabbits. Animals were anesthetized with xylezine (10 mg/kg) and ketamine (40 mg/kg) IV and positioned over a gamma camera (GE Starcam; LEAP collimator). A bolus of $^{99m}$Tc-TMPI (1.5 mCi) was then injected via an ear vein. Planar images were collected for 60 sec/frame up to 1 hour. Energy discrimination was provided by 20% windows centered over the 140 KeV photopeak of $^{99m}$Tc. Each image was corrected on-line for camera nonuniformity with a 300 million count flood and stored at a digital resolution of 64×64. No attenuation or scatter correction was used. Time-activity curves were generated by placing a region-of-interest over each organ and expressing activity in CPM/pixel.
Figure 10B:
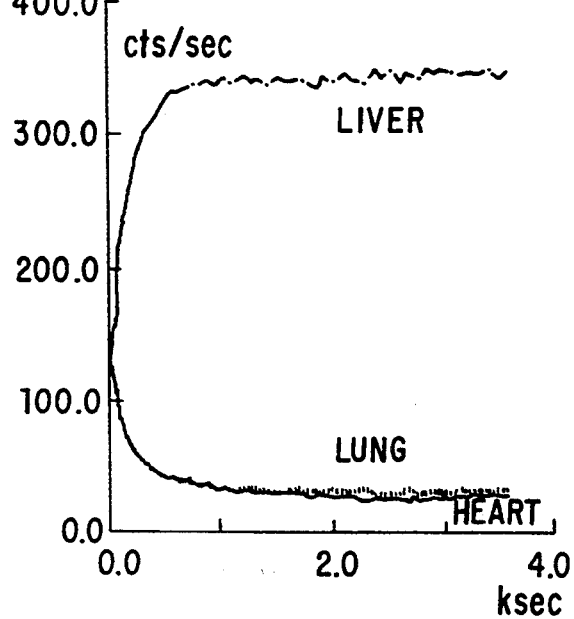
Figure 10C:
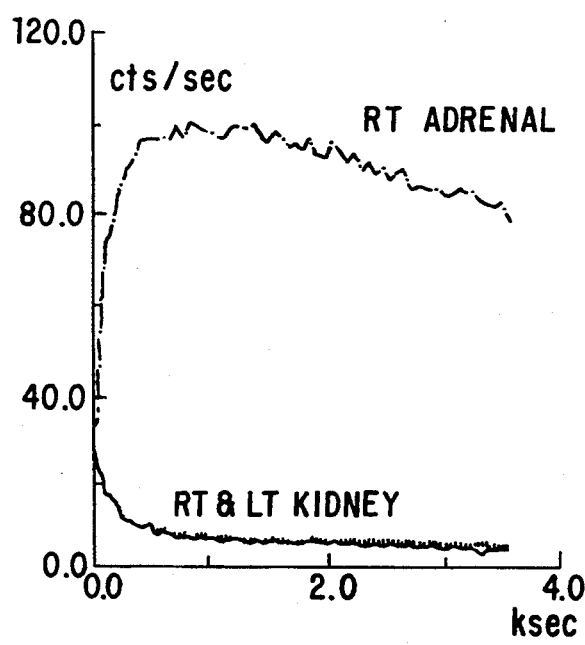
Figure 10D:

The net accumulation at 60 minutes of Tc-TMPI was compared in cultured heart and 77A cells. Note the 5-fold increased accumulation of the complex in the P-glycoprotein-enriched 77A cells consistent with binding of the complex to P-glycoprotein. (FIG. 9).

EXAMPLE 12

The binding in vivo of $^{99m}$Tc-TMPI was assayed by scintigraphic images of adult rabbits. Planar images show high $^{99m}$Tc-TMPI binding in normal tissues known to express high levels of P-glycoprotein such as liver, adrenals, bone marrow, and (to a lesser degree) lung and kidney (Fojo et al., *Proc. Natl. Acad. Sci. USA* 84:265 (1987)). Note the lack of binding in tissues known to express low levels of P-glycoprotein such as heart and skeletal muscle. (FIG. 10). Because Tc-isonitrile complexes are chemically identical to Re-isonitrile complexes (Nicolini, M. et al., (eds.), *Tc and Re in Chemistry and Nuclear Medicine*, Cortina International, Verona, Italy (1986), these data, in effect, show the (*in vivo*) biodistribution.

What is new and claimed and intended to be covered by a Letters Patent of the United States is:

1. A method for increasing the accumulation of a compound in a cell wherein said cell overexpresses an ATP-binding cassette transport protein and wherein said compound is transported by an ATP-binding cassette transport protein, said method comprising coadministering said compound and a (R-isonitrile) metal complex to said cell, wherein said complex is in an amount effective to increase the accumulation of said compound, and wherein R is selected from tile group consisting of alkyl, substituted alkyl, aryl, and substituted aryl.

2. The method of claim 1, wherein the ATP-binding cassette transport protein is the protein product of the multidrug resistance gene.

3. A method of killing a cell that overexpresses an ATP-binding cassette transport protein, said method comprising coadministering a cytotoxic agent in an amount effective to kill said cell and a (R-isonitrile) metal complex, wherein said complex is in an amount effective to cause the accumulation of said effective amount of said cytotoxic agent, wherein said agent is transported by said ATP-binding cassette transport protein, and wherein R is selected from the group consisting of alkyl, substituted alkyl, aryl, and substituted aryl.

4. The method of claim 3 wherein the ATP binding cassette transport protein is the protein product of the multidrug resistance transport gene.

5. A method of reversing the multidrug resistance phenotype in a multidrug resistant tumor cell comprising coadministering a chemotherapeutic compound in an amount effective to kill said multidrug resistant tumor cell, and a (R-isonitrile) metal complex, in an amount effective to cause the accumulation of said effective amount of said compound, to a patient bearing said tumor cell, and wherein R is selected from the group consisting of alkyl, substituted alkyl, aryl, and substituted aryl.

6. The method of any one of claims 1–5 wherein said complex is a hexakis (arylisonitrile) metal complex, wherein said metal is selected from the group consisting of technetium and rhenium.

7. The method of claim 6 wherein said aryl isonitrile is selected from the group consisting of 3-, 4-, 5-trimethoxyphenylisonitrile; 3-, 4-dimethoxybenzylisonitrile; 3, 5-dimethoxybenzylisonitrile; 4-methoxyphenethylisonitrile; acetylphenylisonitrile; and 3, 4-dimethoxyphenethylisonitrile.

8. The method of claim 6 wherein said R-isonitrile metal complex is selected from the group consisting of benzyl, phenyl, substituted benzyl, and substituted phenyl.

* * * * *